(12) United States Patent
Bae et al.

(10) Patent No.: US 9,683,172 B2
(45) Date of Patent: *Jun. 20, 2017

(54) LIQUID CRYSTAL COMPOSITION AND LIQUID CRYSTAL DISPLAY INCLUDING THE SAME

(71) Applicant: Samsung Display Co., Ltd., Yongin-si (KR)

(72) Inventors: Ji Hong Bae, Yongin-si (KR); Keun Chan Oh, Cheonan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/997,882

(22) Filed: Jan. 18, 2016

(65) Prior Publication Data

US 2016/0257881 A1 Sep. 8, 2016

(30) Foreign Application Priority Data

Mar. 6, 2015 (KR) ......................... 10-2015-0031623

(51) Int. Cl.
*G02F 1/1333* (2006.01)
*C09K 19/34* (2006.01)
(Continued)

(52) U.S. Cl.
CPC .......... *C09K 19/3402* (2013.01); *C07C 13/19* (2013.01); *C07C 15/50* (2013.01);
(Continued)

(58) Field of Classification Search
CPC ................ C09K 19/3402; C09K 19/32; C09K 2019/3422; C09K 2019/0466;
(Continued)

(56) References Cited

U.S. PATENT DOCUMENTS 7,335,403 B2 2/2008 Klasen-Memmer et al.
7,704,567 B2 4/2010 Klasen-Memmer et al.
(Continued)

FOREIGN PATENT DOCUMENTS

CN 1714137 12/2005
CN 103194242 7/2013
(Continued)

OTHER PUBLICATIONS

Miyazawa et al. "Synthesis and Some Physical Properties of Bicyclohexanes Having Fluoro Substituted Alkyl Moiety", Molecular Crystals and Liquid Crystals Science and Technology, vol. 260(1), 1995, pp. 277-286.

*Primary Examiner* — Geraldina Visconti
(74) *Attorney, Agent, or Firm* — H.C. Park & Associates, PLC

(57) ABSTRACT

A liquid crystal composition includes at least one polar liquid crystal compound represented by Chemical Formula PI-1 to PI-4:

Chemical Formula PI-1

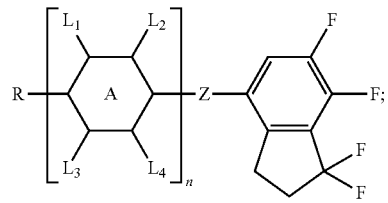

Chemical Formula PI-2

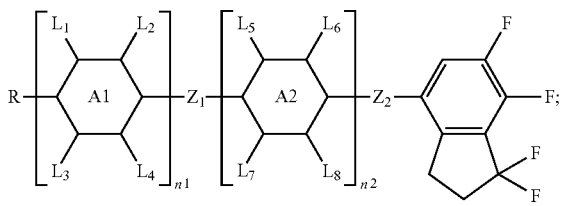

Chemical Formula PI-3

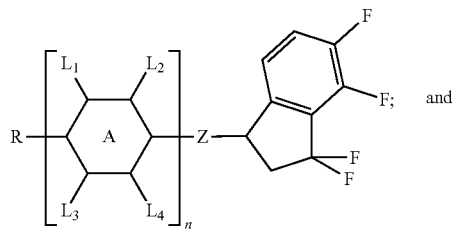

and

Chemical Formula PI-4

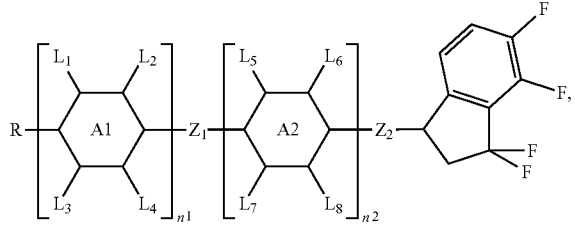

in which each n, n1, and n2 in Chemical Formula PI-1 to PI-4 is any one of 1, 2, and 3, in Chemical Formula PI-1 to PI-4, each A, A1, and A2 includes one of (Continued)

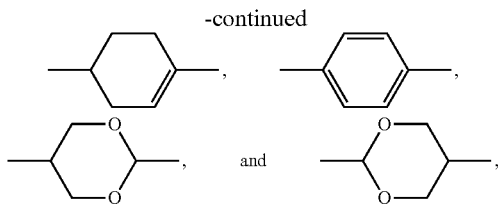

each L1 to L8 includes one of —H, —F, —Cl, —OCF$_3$, —CF$_3$, —CH$_2$F, and —CHF$_2$, each Z, Z1, and Z2 includes one of single bond, —COO—, —OCO—, —CF$_2$O—, —OCF$_2$—, —CH$_2$O—, —OCH$_2$—, —SCH$_2$—, —CH$_2$S—, —CH$_2$CH$_2$—, —C$_2$F$_4$—, —CH$_2$—CF$_2$—, —CF$_2$CH$_2$—, —(CH$_2$)$_z$— (z is 1 to 3), —CH=CH—, —CF=CF—, —CH=CF—, —CF=CH—, —C≡C—, and —CH=CHCH$_2$O—, and R includes one of hydrogen, halogen, a cyano group, alkyl group, and an alkoxy group including 1 to 12 carbon atoms.

14 Claims, 3 Drawing Sheets

(51) Int. Cl.
| | |
|---|---|
| C09K 19/32 | (2006.01) |
| C07C 25/22 | (2006.01) |
| C07C 25/13 | (2006.01) |
| C07C 13/19 | (2006.01) |
| C07C 15/50 | (2006.01) |
| C07C 43/225 | (2006.01) |
| C09K 19/04 | (2006.01) |
| C09K 19/12 | (2006.01) |
| C09K 19/30 | (2006.01) |

(52) U.S. Cl.
CPC .............. *C07C 25/13* (2013.01); *C07C 25/22* (2013.01); *C07C 43/225* (2013.01); *C09K 19/32* (2013.01); *C07C 2101/14* (2013.01); *C07C 2102/08* (2013.01); *C09K 2019/0466* (2013.01); *C09K 2019/123* (2013.01); *C09K 2019/301* (2013.01); *C09K 2019/3016* (2013.01); *C09K 2019/3019* (2013.01); *C09K 2019/3021* (2013.01); *C09K 2019/3422* (2013.01)

(58) Field of Classification Search
CPC ........ C09K 2019/123; C09K 2019/301; C09K 2019/3016; C09K 2019/3019; C09K 2019/3021; C07C 25/22; C07C 25/13; C07C 13/19; C07C 15/50; C07C 43/225
USPC ........................ 252/299.01, 299.62; 349/182
See application file for complete search history.

(56) References Cited

U.S. PATENT DOCUMENTS

| | | | |
|---|---|---|---|
| 2011/0101270 A1 | 5/2011 | Manabe et al. | |
| 2015/0267117 A1* | 9/2015 | Kim .................... | C09K 19/3003 349/139 |
| 2016/0200978 A1* | 7/2016 | Bae .................... | C09K 19/3402 349/123 |

FOREIGN PATENT DOCUMENTS

| | | |
|---|---|---|
| CN | 103351274 | 10/2013 |
| CN | 103351275 | 10/2013 |
| DE | 10354404 | 6/2004 |
| EP | 1563035 | 8/2005 |
| JP | 2006-507387 | 3/2006 |
| KR | 10-2007-0017967 | 2/2007 |
| KR | 10-2011-0005272 | 1/2011 |
| KR | 10-2011-0039477 | 4/2011 |
| WO | 2004-048500 | 6/2004 |

* cited by examiner

LIQUID CRYSTAL COMPOSITION AND LIQUID CRYSTAL DISPLAY INCLUDING THE SAME

CROSS-REFERENCE TO RELATED APPLICATION

This application claims priority from and the benefit of Korean Patent Application No. 10-2015-0031623, filed on Mar. 6, 2015, which is hereby incorporated by reference for all purposes as if fully set forth herein.

BACKGROUND

Field

Exemplary embodiments of the present invention relate to a liquid crystal composition and a liquid crystal display including the same.

Discussion of the Background

A liquid crystal display, among flat panel displays, includes two display panels facing each other, a liquid crystal layer interposed therebetween, a field generating electrode, such as a pixel electrode and a common electrode positioned on at least one of the two display panels, and the like.

The liquid crystal display generates an electric field in the liquid crystal layer by applying voltage to the field generating electrodes, and determines a direction of liquid crystal molecules of the liquid crystal layer by the generated electric field, thus controlling polarization of incident light to display images.

In the liquid crystal display, a liquid crystal composition may be important in obtaining a desired image by adjusting transmittance of light. Particularly, as the purpose of the liquid crystal display is diversified, various characteristics, such as low voltage driving, a high voltage holding ratio (VHR), a wide viewing angle characteristic, a wide motion temperature range, and a high-speed response characteristic may be required.

In order to implement high-speed response characteristic and the like of the liquid crystal display, research has been performed to improve properties of the liquid crystal composition, such as rotation viscosity, a refractive index, and an elastic coefficient thereof.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments of the present invention provide a liquid crystal composition that may increase reliability while having a high dielectric constant, and a liquid crystal display including the same.

Additional aspects will be set forth in the detailed description which follows, and, in part, will be apparent from the disclosure, or may be learned by practice of the inventive concept.

According to an exemplary embodiment of the present invention, a liquid crystal composition includes at least one of the polar liquid crystal compounds represented by Chemical Formula PI-1 to Chemical Formula PI-4:

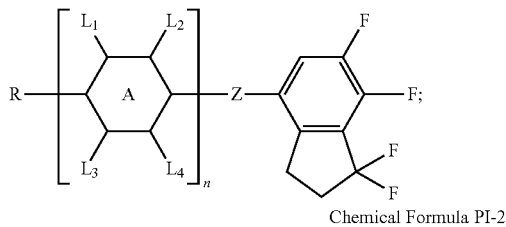

Chemical Formula PI-1

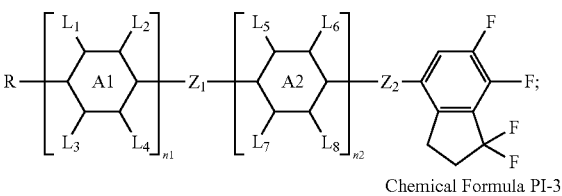

Chemical Formula PI-2

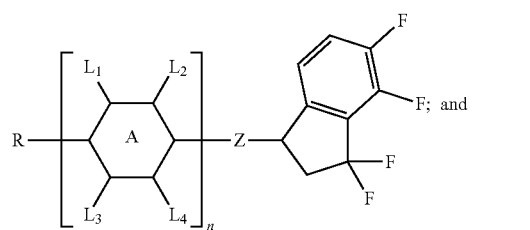

Chemical Formula PI-3

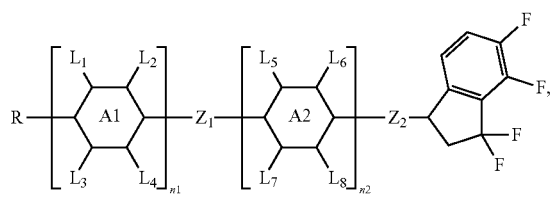

Chemical Formula PI-4 in which each of n, n1, and n2 in Chemical Formula PI-1 to Chemical Formula PI-4 may be any one 1, 2, and 3, in Chemical Formula PI-1 to Chemical Formula PI-4, each of A, A1, and A2 includes one of

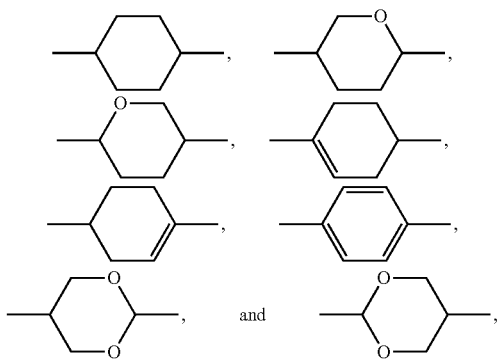

in Chemical Formula PI-1 to Chemical Formula PI-4, each of L1 to L8 includes one of —H, —F, —Cl, —OCF$_3$, —CF$_3$, —CH$_2$F, and —CHF$_2$, in Chemical Formula PI-1 to Chemical Formula PI-4, each of Z, Z1, and Z2 includes one of single bond, —COO—, —OCO—, —CF$_2$O—, —OCF$_2$—, —CH$_2$O—, —OCH$_2$—, —SCH$_2$—, —CH$_2$S—, —CH$_2$CH$_2$—, —C$_2$F$_4$—, —CH$_2$—CF$_2$—, —CF$_2$CH$_2$—, —(CH$_2$)$_z$— (z is 1 to 3), —CH═CH—, —CF═CF—, —CH═CF—, —CF═CH—, —C═C—, and —CH═CHCH$_2$O—, and in Chemical Formula PI-1 to Chemical Formula PI-4, R includes one of hydrogen, halogen, a cyano group, an alkyl group, and an alkoxy group including 1 to 12 carbon atoms.

Compounds represented by Chemical Formula PI-1 to Chemical Formula PI-4 may be 1 wt % to 10 wt % of the entire liquid crystal composition.

Dielectric anisotropy Δ∈ of polar liquid crystal compounds represented by Chemical Formula PI-1 to Chemical Formula PI-4 may be in a range of 10 to 30.

The liquid crystal composition may further include at least one of the alkenyl-based liquid crystal compounds represented by Chemical Formula A-1 to Chemical Formula A-7:

Chemical Formula A-1

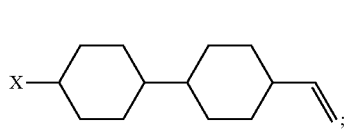

Chemical Formula A-2

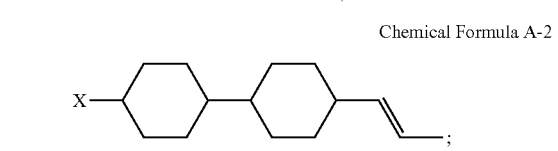

Chemical Formula A-3

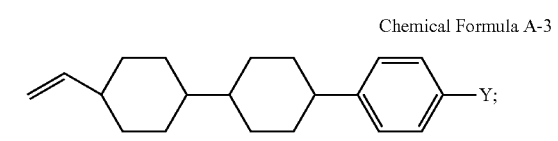

Chemical Formula A-4

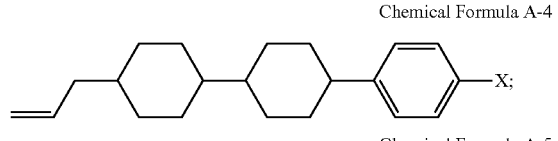

Chemical Formula A-5

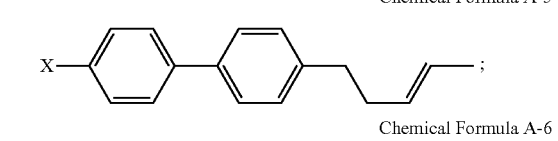

Chemical Formula A-6

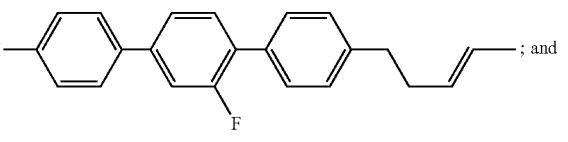

Chemical Formula A-7

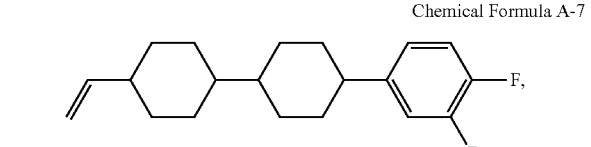

in which each of X and Y in Chemical Formula A-1 to Chemical Formula A-7 may include one of an alkyl group having 1 to 5 carbon atoms.

The liquid crystal composition may further include at least one of the neutral compounds represented by Chemical Formula N-1 to Chemical Formula N-5:

Chemical Formula N-1

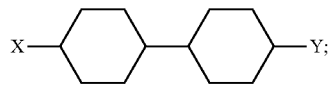

Chemical Formula N-2

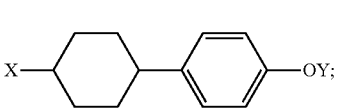

Chemical Formula N-3

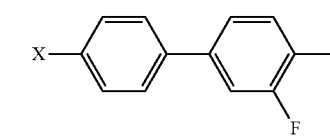

Chemical Formula N-4

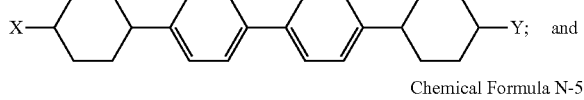

and

Chemical Formula N-5

in which each of X and Y in the Chemical Formula N-1 to Chemical Formula N-5 may include one of an alkyl group having 1 to 5 carbon atoms.

The liquid crystal composition may further include at least one of the polar compounds represented by Chemical Formula P-1 to Chemical Formula P-11:

Chemical Formula P-1

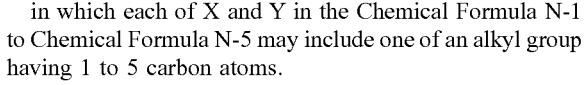

Chemical Formula P-2

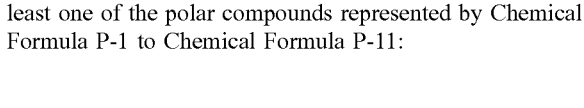

Chemical Formula P-3

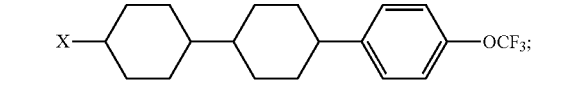

Chemical Formula P-4

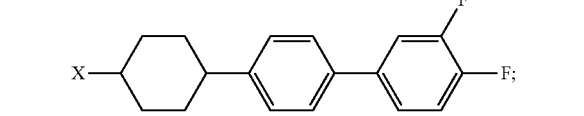

-continued

Chemical Formula P-5
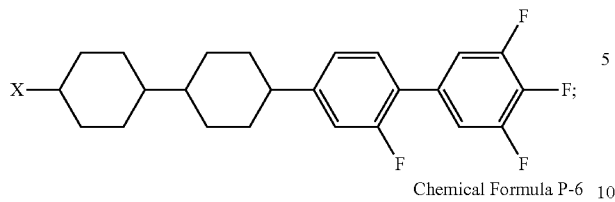

Chemical Formula P-6
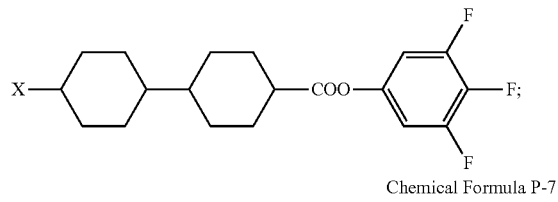

Chemical Formula P-7
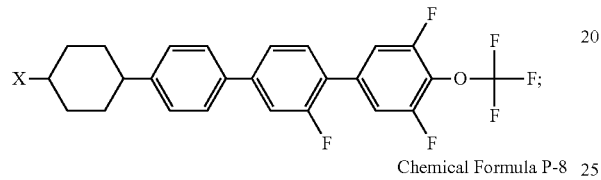

Chemical Formula P-8
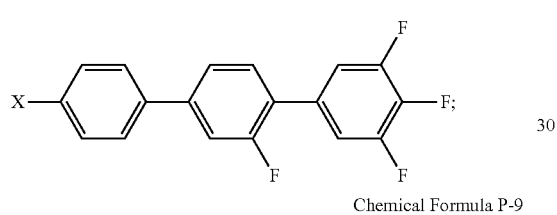

Chemical Formula P-9
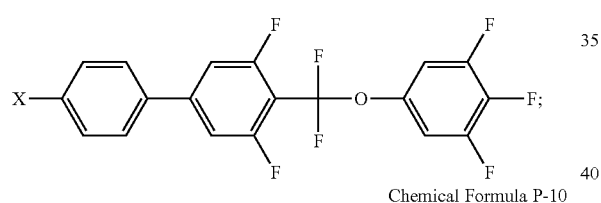

Chemical Formula P-10
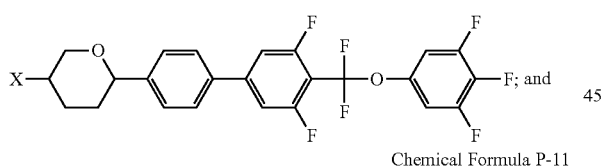

Chemical Formula P-11
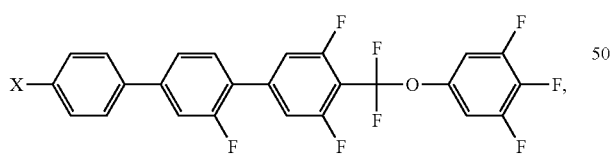

in which each of X and Y in the Chemical Formula P-1 to Chemical Formula P-11 may include one of an alkyl group having 1 to 5 carbon atoms.

Dielectric anisotropy of the liquid crystal composition may be in a range of 5 to 20.

According to an exemplary embodiment of the present invention, a liquid crystal display includes a first substrate, a second substrate facing the first substrate, a liquid crystal layer disposed between the first substrate and the second substrate, in which the liquid crystal layer includes at least one of the polar liquid crystal compounds represented by Chemical Formula PI-1 to Chemical Formula PI-4:

Chemical Formula PI-1
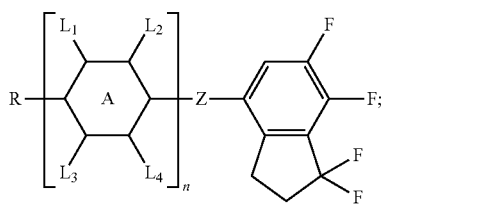

Chemical Formula PI-2
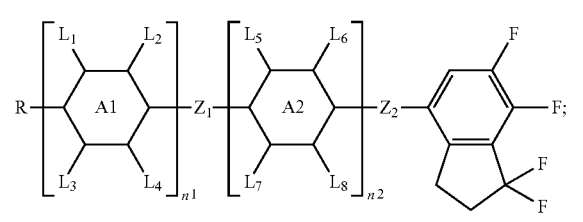

Chemical Formula PI-3
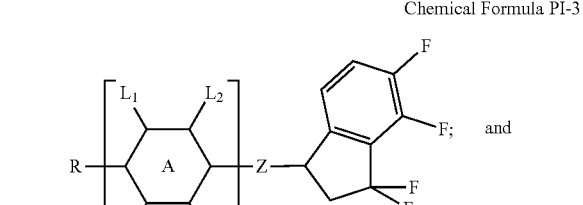

and

Chemical Formula PI-4
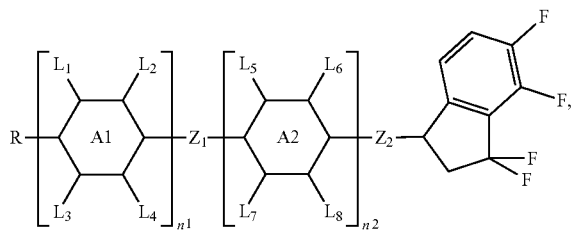

in which in Chemical Formula PI-1 to Chemical Formula PI-4, each of n, n1, and n2 may be any one of 1, 2 and 3, each of Z, Z1, and Z2 may include one of single bond, —COO—, —OCO—, —CF$_2$O—, —OCF$_2$—, —CH$_2$O—, —OCH$_2$—, —SCH$_2$—, —CH$_2$S—, —CH$_2$CH$_2$—, —C$_2$F$_4$—, —CH$_2$—CF$_2$—, —CF$_2$CH$_2$—, —(CH$_2$)$_z$— (z is 1 to 3), —CH═CH—, —CF═CF—, —CH═CF—, —CF═CH—, —C═C—, and —CH═CHCH$_2$O—, each of L1 to L8 may include one of —H, —F, —Cl, —OCF$_3$, —CF$_3$, —CH$_2$F, and —CHF$_2$, in Chemical Formula PI-1 to Chemical Formula PI-4, each of A, A1, and A2 includes one of

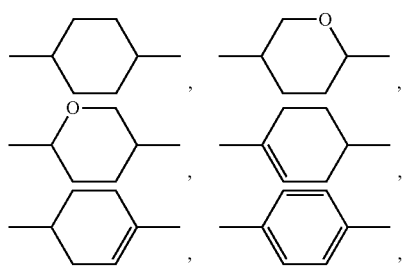

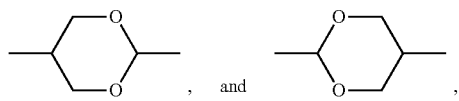, and and in Chemical Formula PI-1 to Chemical Formula PI-4, R includes one of hydrogen, halogen, a cyano group, an alkyl group, and an alkoxy group including 1 to 12 carbon atoms.

Compounds represented by Chemical Formula PI-1 to Chemical Formula PI-4 may be 1 wt % to 10 wt % of the entire liquid crystal composition.

Dielectric anisotropy $\Delta\varepsilon$ of the polar liquid crystal compounds represented by Chemical Formula PI-1 to Chemical Formula PI-4 may be in a range of 10 to 30.

The liquid crystal layer may further include at least one of the alkenyl-based liquid crystal compounds represented by Chemical Formula A-1 to Chemical Formula A-7:

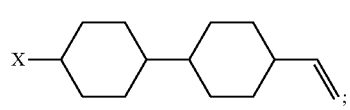

Chemical Formula A-1

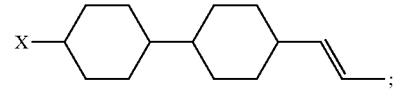

Chemical Formula A-2

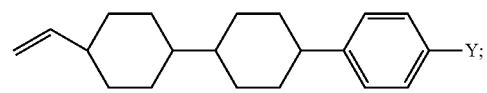

Chemical Formula A-3

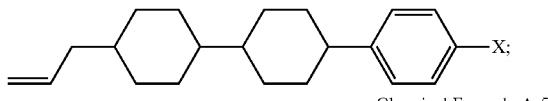

Chemical Formula A-4

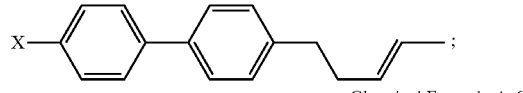

Chemical Formula A-5

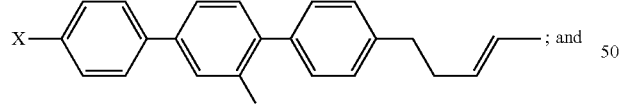

Chemical Formula A-6

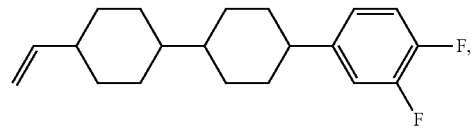

Chemical Formula A-7 in which each of X and Y in Chemical Formula A-1 to Chemical Formula A-7 may include one alkyl group having 1 to 5 carbon atoms.

The liquid crystal layer may further include at least one of the neutral compounds represented by Chemical Formula N-1 to Chemical Formula N-5:

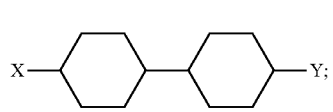

Chemical Formula N-1

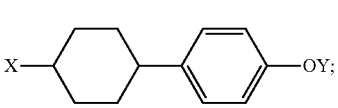

Chemical Formula N-2

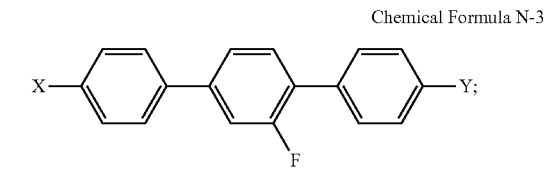

Chemical Formula N-3

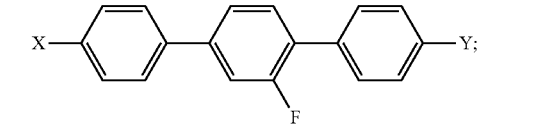

Chemical Formula N-4

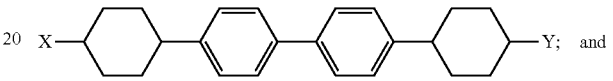

Chemical Formula N-5 in which each of X and Y in Chemical Formula N-1 to Chemical Formula N-5 may include one alkyl group having 1 to 5 carbon atoms.

The liquid crystal display may further include polar compounds represented by Chemical Formula P-1 to Chemical Formula P-11:

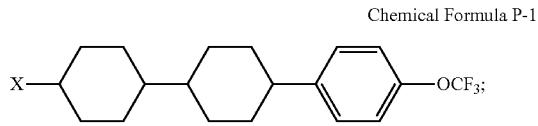

Chemical Formula P-1

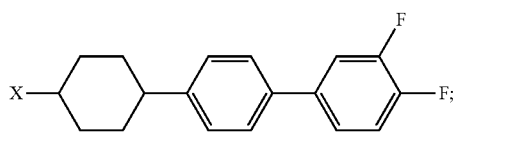

Chemical Formula P-2

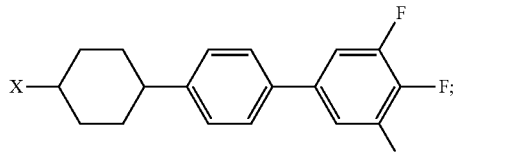

Chemical Formula P-3

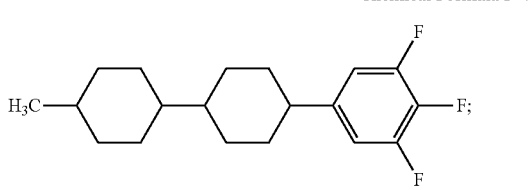

Chemical Formula P-4

-continued

Chemical Formula P-5

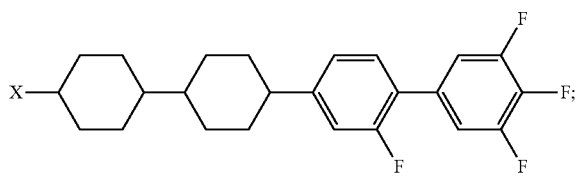

Chemical Formula P-6

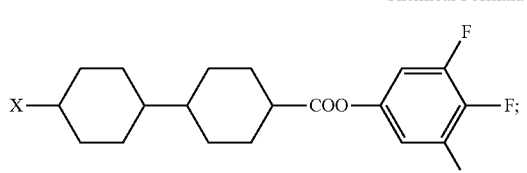

Chemical Formula P-7

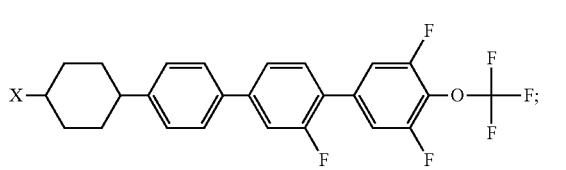

Chemical Formula P-8

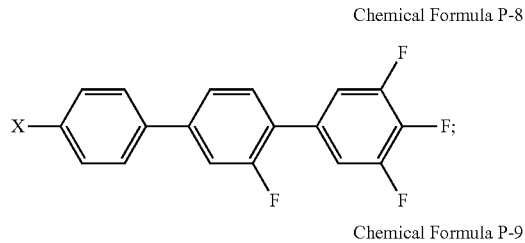

Chemical Formula P-9

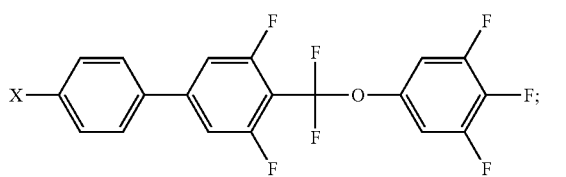

Chemical Formula P-10

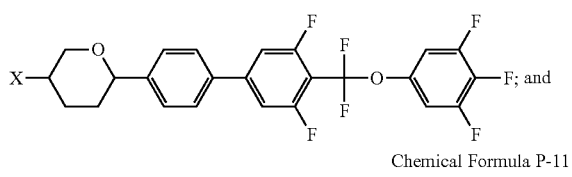

Chemical Formula P-11

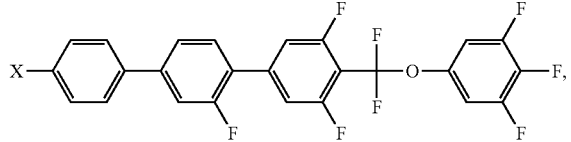

in which each of X and Y in Chemical Formula P-1 to Chemical Formula P-11 include one alkyl group having 1 to 5 carbon atoms.

Dielectric anisotropy of the liquid crystal composition included in the liquid crystal layer may be in a range of 5 to 20.

According to the exemplary embodiments of the present invention, a liquid crystal display is formed using a liquid crystal composition having a positive polarity, and have low voltage characteristics with improved reliability.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION OF THE ILLUSTRATED EMBODIMENTS

Figure 1:
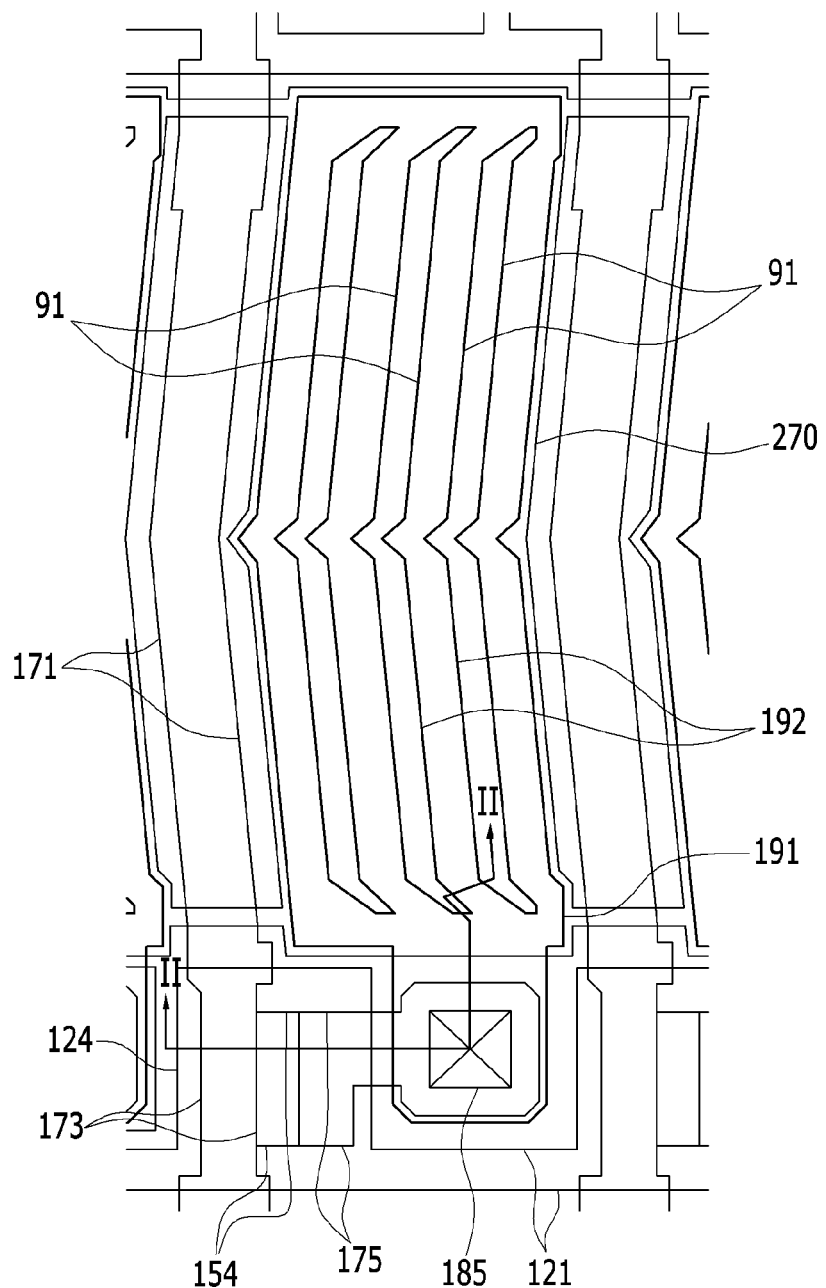
FIG. 1 is a top plan view of a liquid crystal display according to an exemplary embodiment of the present invention.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

In the accompanying figures, the size and relative sizes of layers, films, panels, regions, etc., may be exaggerated for clarity and descriptive purposes. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. Like numbers refer to like elements throughout. As used herein, the term "and/or" includes any and all combinations of one or more of the associated listed items.

Although the terms first, second, etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Various exemplary embodiments are described herein with reference to sectional illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not be construed as limited to the particular illustrated shapes of regions, but are to include deviations in shapes that result from, for instance, manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the drawings are schematic in nature and their shapes are not intended to illustrate the actual shape of a region of a device and are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

A liquid crystal composition according to an exemplary embodiment of the present invention includes at least one polar liquid crystal compound represented by Chemical Formula PI-1 to Chemical Formula PI-4.

Chemical Formula PI-1

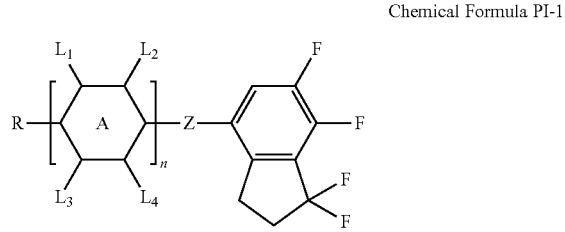

Chemical Formula PI-2

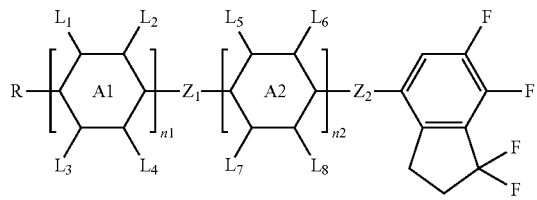

Chemical Formula PI-3

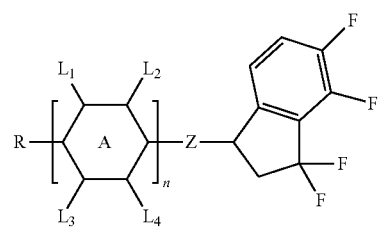

Chemical Formula PI-4

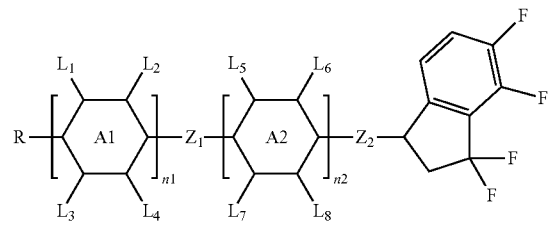

In Chemical Formula PI-1 to Chemical Formula PI-4, each of n, $n_1$, and $n_2$ may be any one of 1, 2, and 3.

In Chemical Formula PI-1 to Chemical Formula PI-4, each of A, A1, and A2 may be one of

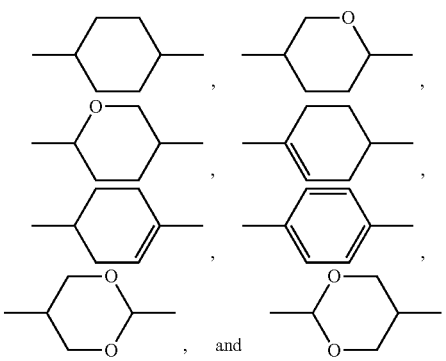

In Chemical Formula PI-1 to Chemical Formula PI-4, each of L1 to L8 may be one of H, F, Cl, $OCF_3$, $CF_3$, $CH_2F$, and $CHF_2$.

In Chemical Formula PI-1 to Chemical Formula PI-4, Z, Z1, and Z2 may be one of single bond, —COO—, —OCO—, —$CF_2$O—, —O$CF_2$—, —$CH_2$O—, —O$CH_2$—, —S$CH_2$—, —$CH_2$S—, —$CH_2CH_2$—, —$C_2F_4$—, —$CH_2CF_2$—, —$CF_2CH_2$—, —$(CH_2)_Z$— (z is 1 to 3), —CH═CH—, —CF═CF—, —CH═CF—, —CF═CH—, —C≡C—, and —CH═CH$CH_2$O—.

In Chemical Formula PI-1 to Chemical Formula PI-4, R may independently include one of hydrogen, halogen, a cyano group, an alkyl group, and an alkoxy group including 1 to 12 carbon atoms.

In the present exemplary embodiment, dielectric anisotropy ΔE of polar liquid crystal compounds represented by Chemical Formula PI-1 to Chemical Formula PI-4 may be in a range of 10 to 30.

Specifically, the compounds represented by Chemical Formula PI-1 to Chemical Formula PI-4 may include at least one of the compounds represented by Chemical Formula 1 to Chemical Formula 6.

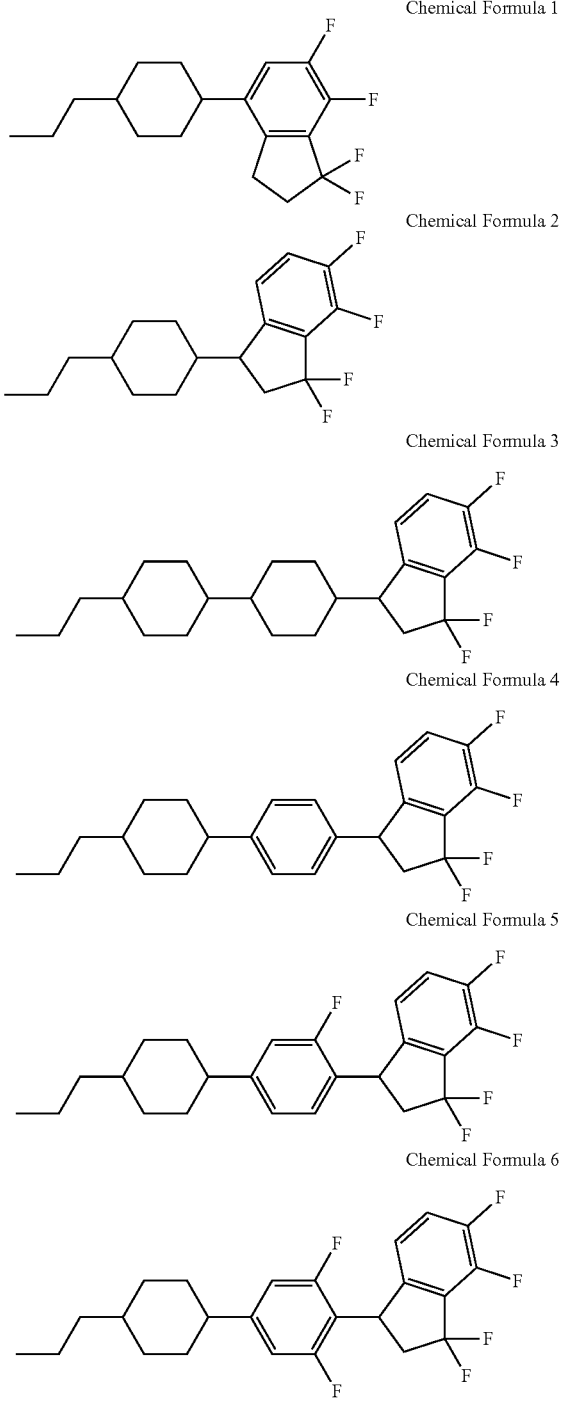

Chemical Formula 1

Chemical Formula 2

Chemical Formula 3

Chemical Formula 4

Chemical Formula 5

Chemical Formula 6

A refractive index Δn of Chemical Formula 1 is about 0.08 and dielectric anisotropy ΔE is about 15.4. A refractive index Δn of Chemical Formula 2 is about 0.09 and dielectric anisotropy ΔE is about 16.0. A refractive index Δn of Chemical Formula 3 is about 0.13 and dielectric anisotropy ΔE is about 16. A refractive index Δn of Chemical Formula 4 is about 0.16 and dielectric anisotropy ΔE is about 16.8. A refractive index Δn of Chemical Formula 5 is about 0.15 and dielectric anisotropy ΔE is about 14.4. A refractive index Δn of Chemical Formula 6 is about 0.17 and dielectric anisotropy ΔE is about 15.5.

Chemical Formula 1 to Chemical Formula 6 may be respectively formed according to the following composition examples 1 to 6.

Composition Example 1

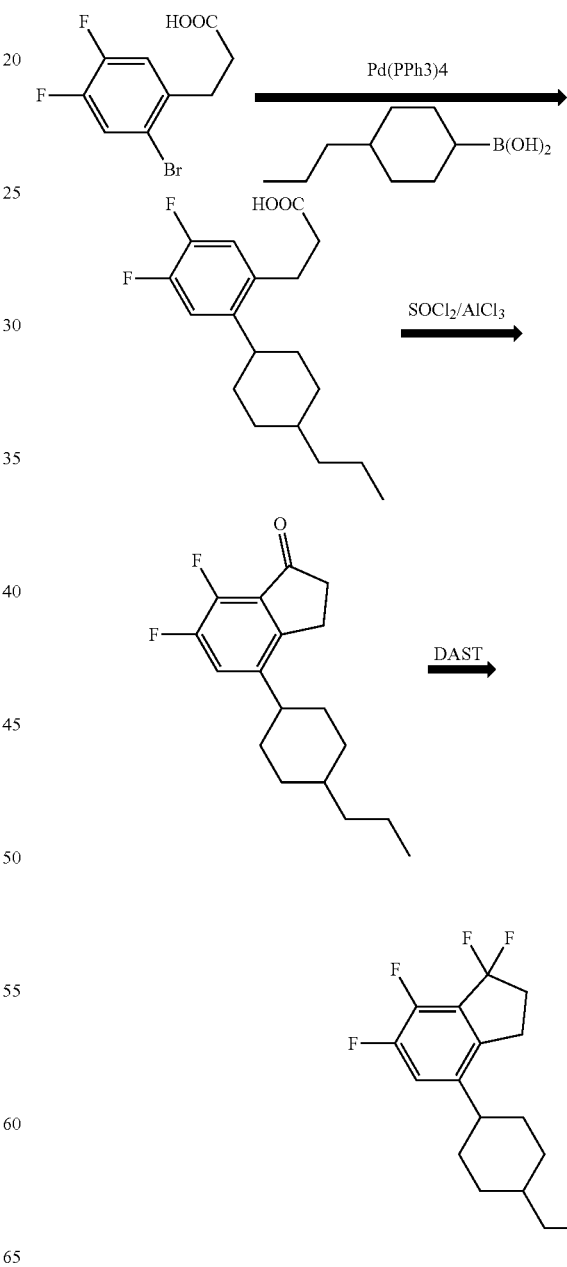

Composition Example 2
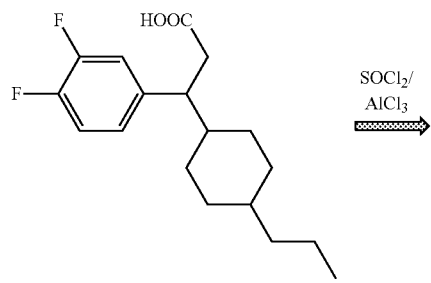
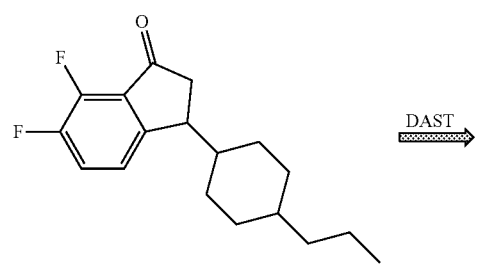
Composition Example 3
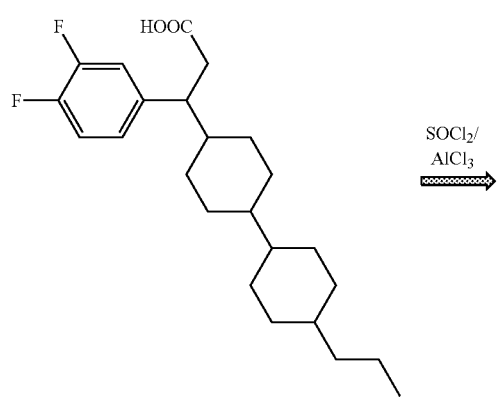
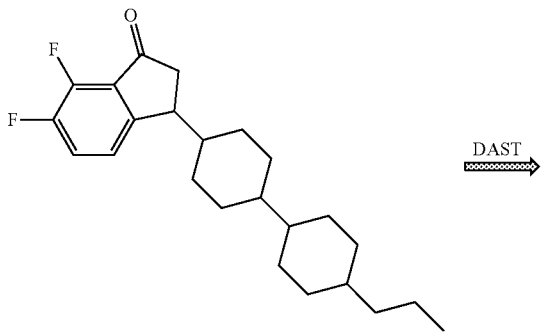
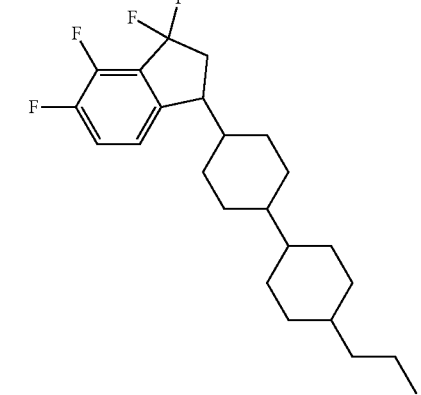
Composition Example 4
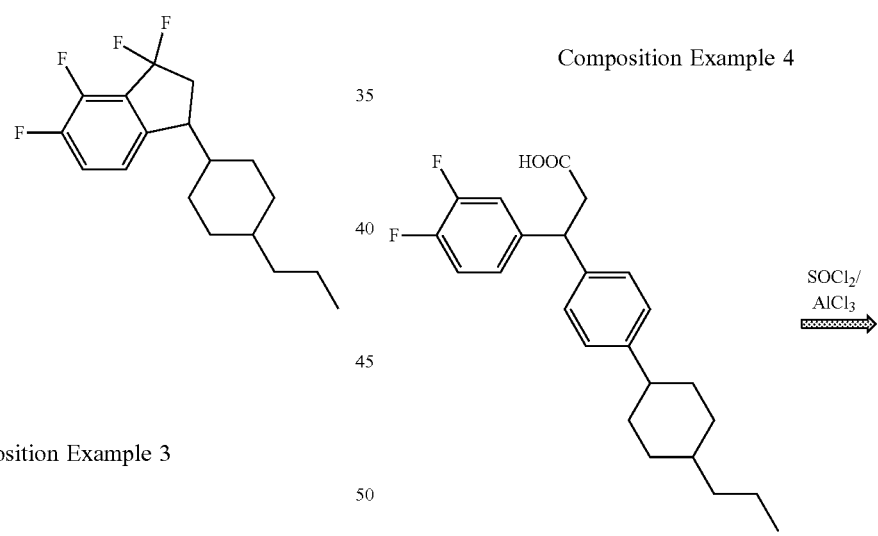
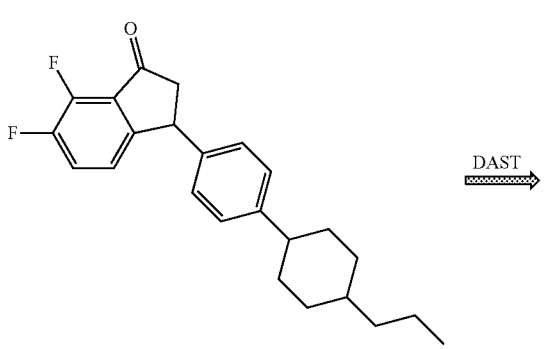

Composition Example 6

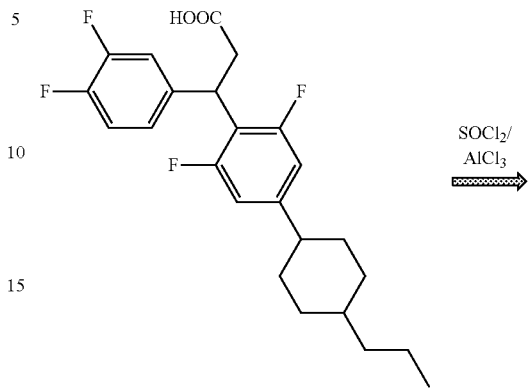

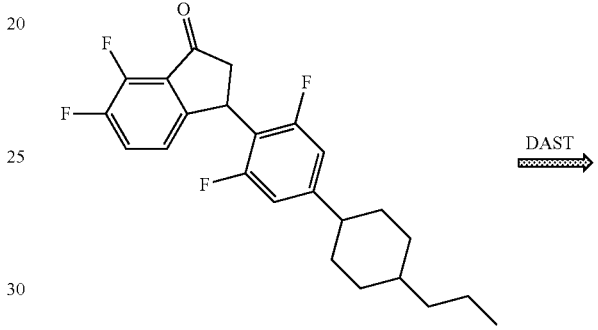

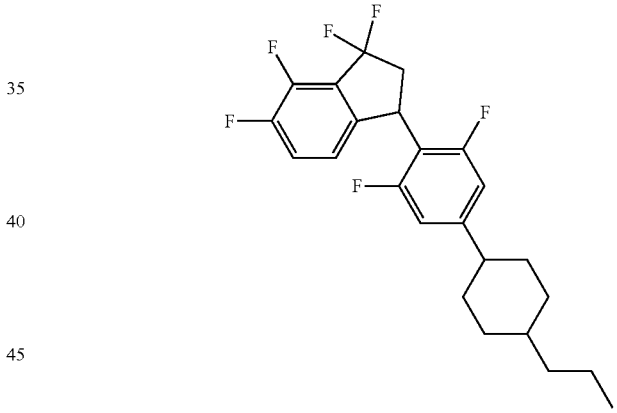

Composition Example 5

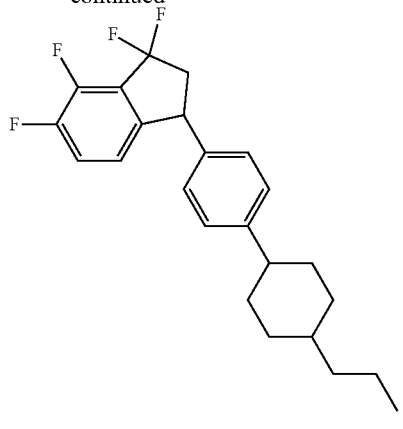

DAST in the composition examples 1 to 6 denotes N,N-diethylaminosulfur trifluoride. In the present exemplary embodiment, DAST may be used as a reagent for fluorine substitution through deoxygenation from carbonyl. For the fluorine substitution of carbonyl, SeF4, DAST DeoxoFluor, TFEDMA (N,N-dimethyl-1,1,2,2-tetrafluorothylamine), XtalFluor-E, which is more stable in a solid state, XtalFluor-M, FluoLead, and the like may be used instead of using DAST.

The compounds represented by Chemical Formula PI-1 to Chemical Formula PI-4 may be included in a content of about 1 to 10 wt % based on the total liquid crystal composition content.

The liquid crystal composition according to the present exemplary embodiment may further include at least one of the alkenyl-based liquid crystal compounds represented by Chemical Formula A-1 to Chemical Formula A-7.

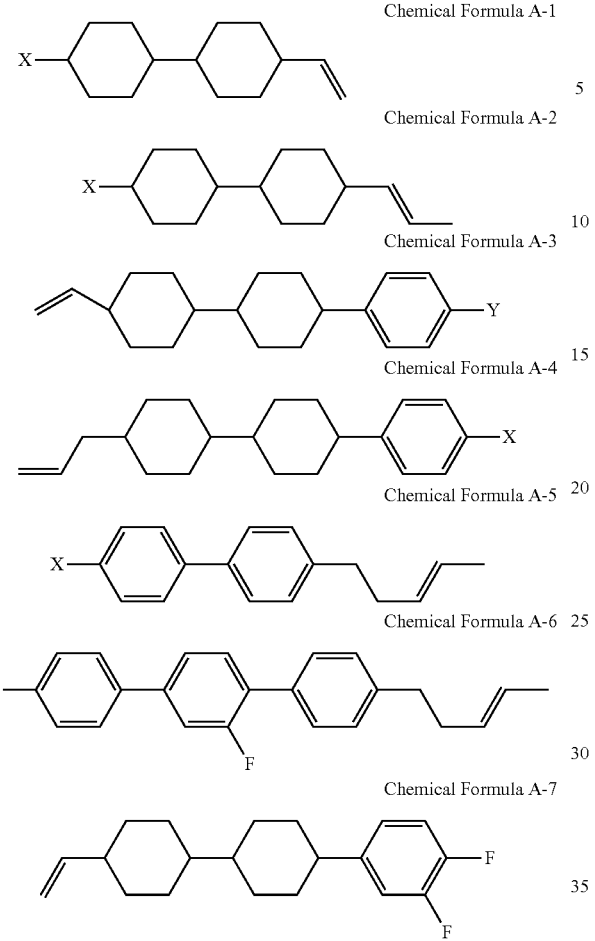

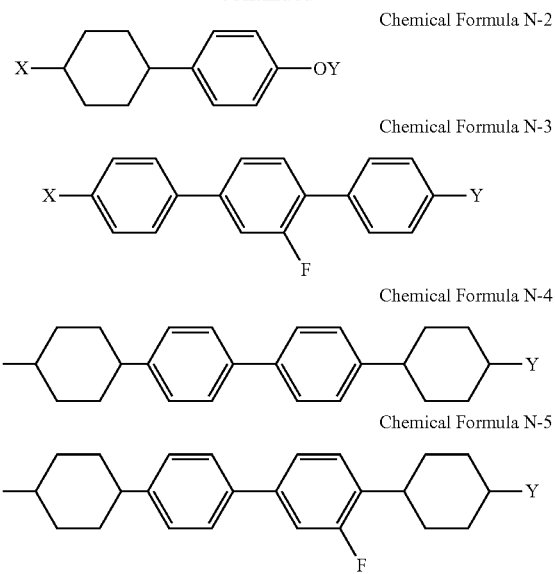

In Chemical Formula A-1 to Chemical Formula A-7, X and Y may respectively include an alkyl group including 1 to 5 carbon atoms. In this case, the compound of Chemical Formula A-1 may have 10 to 45 wt %, the compound of Chemical Formula A-2 may have 3 to 15 wt %, the compound of Chemical Formula A-3 may have 2 to 15 wt %, the compound of Chemical Formula A-4 may have 5 to 10 wt %, the compound of Chemical Formula A-5 may have 2 to 8 wt %, the compound of Chemical Formula A-6 may have 5 to 22 wt %, and the compound of Chemical Formula A-7 may have 2 to 10 wt % based on the entire liquid crystal composition.

According to the present exemplary embodiment, the alkenyl-based liquid crystal compound may be neutral liquid crystal having low viscosity and have a high-speed response characteristic because of the low viscosity.

The liquid crystal composition according to the present exemplary embodiment may further include at least one of the neutral compounds represented by Chemical Formula N-1 to Chemical Formula N-5.

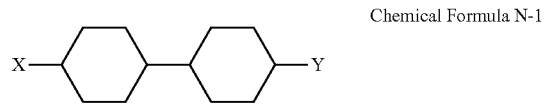

In Chemical Formula N-1 to Chemical Formula N-5, X and Y may respectively include one alkyl group including 1 to 5 carbon atoms. In this case, the compound of Chemical Formula N-1 may have 1 to 5 wt %, the compound of Chemical Formula N-2 may have 5 to 15 wt %, the compound of Chemical Formula N-3 may have 5 to 20 wt %, and the compound of Chemical Formula N-5 may have 2 to 7 wt % based on the total liquid crystal composition content.

The liquid crystal composition according to the present exemplary embodiment may further include at least one of the polar compounds represented by Chemical Formula P-1 to Chemical Formula P-11.

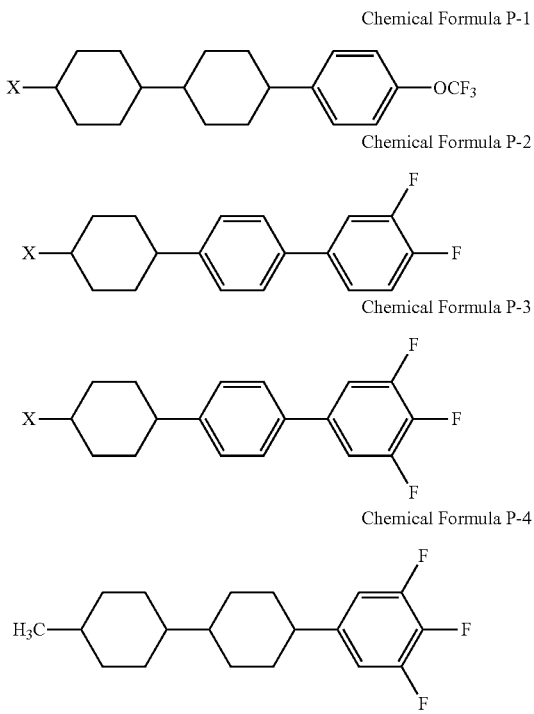

-continued

Chemical Formula P-5

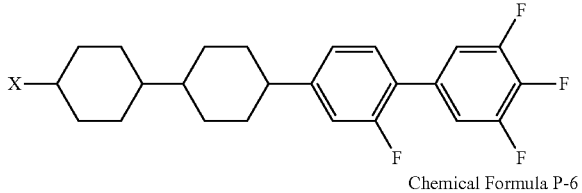

Chemical Formula P-6

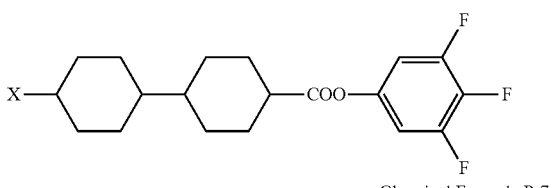

Chemical Formula P-7

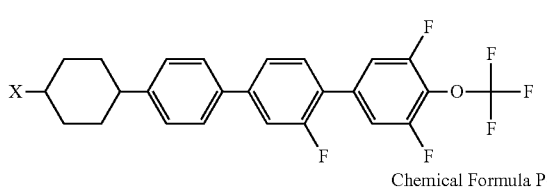

Chemical Formula P-8

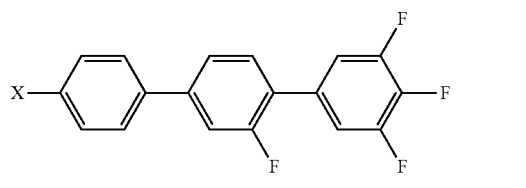

Chemical Formula P-9

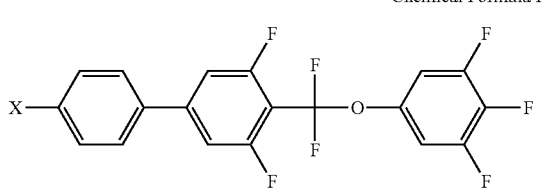

Chemical Formula P-10

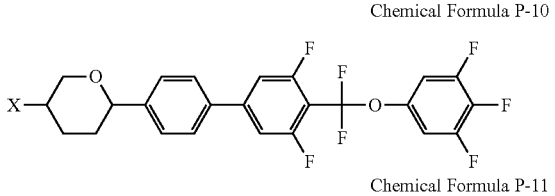

Chemical Formula P-11

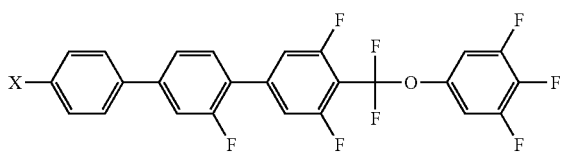

In Chemical Formula P-1 to Chemical Formula P-11, X and Y may respectively include one alkyl group including 1 to 5 carbon atoms. In this case, the compound of Chemical Formula P-1 may have 5 to 10 wt %, the compound of Chemical Formula P-2 may have 5 to 15 wt %, the compound of Chemical Formula P-3 may have 1 to 5 wt %, the compound of P-4 may have 5 to 15 wt %, the compound of Chemical Formula P-5 may have 0.5 to 5 wt %, the compound of Chemical Formula P-6 may have 2 to 15 wt %, the compound of Chemical Formula P-7 may have 2 to 7 wt %, the compound of Chemical Formula P-8 may have 5 to 20 wt %, the compound of Chemical Formula P-9 may have 2 to 15 wt %, the compound of Chemical Formula P-10 may have 5 to 10 wt %, and the compound of Chemical Formula P-11 may have 3 to 10 wt % based on the content of the entire liquid crystal composition.

Dielectric anisotropy $\Delta\in$ of the liquid crystal composition according to the present exemplary embodiment may be in a range of 5 to 20.

The liquid crystal composition according to the present exemplary embodiment may further include an antioxidant. The antioxidant may prevent oxidation of the alkenyl-based compound or the alkoxy-based compound that may occur during or after manufacturing a liquid crystal display, without deteriorating light characteristic of the liquid crystal display. More particularly, the antioxidant may prevent primary oxidation of the alkenyl-based compound and the alkoxy-based compound due to light, heat, and an initiator.

The antioxidant according to the present exemplary embodiment may be at least one of alkylated monophenol, alkylthio methyl phenol, hydroquinone and alkylated hydroquinone, tocopherol, hydroxylated thiodiphenyl ether, alkylidene bisphenol, O-, N- and S-benzyl compound, hydroxy-benzylated malonate, aromatic hydroxybenzyl compound, benzylphosphosnate, acylamino phenol, monovalent or polyvalent alcohol, ester of monovalent or polyvalent alcohol with β-(3,5-di-tert-butyl-4-hydroxyphenyl)-propionic acid, ester of monovalent or polyvalent alcohol with β-(5-tert-butyl-4-hydroxy-3-methylphenyl)-propionic acid, ester of monovalent or polyvalent alcohol with β-(3,5-dicyclohexyl-4-hydroxyphenyl)-propionic acid, ester of monovalent or polyvalent alcohol with 3,5-di-tert-butyl-4-hydroxyphenyl acetic acid, amide of β-(3,5-di-tert-butyl-4-hydroxyphenyl) propionic acid, ascorbic acid, and an amine antioxidant.

Hereinafter, a liquid crystal display including the above-described liquid crystal composition will be described.

Figure 2:
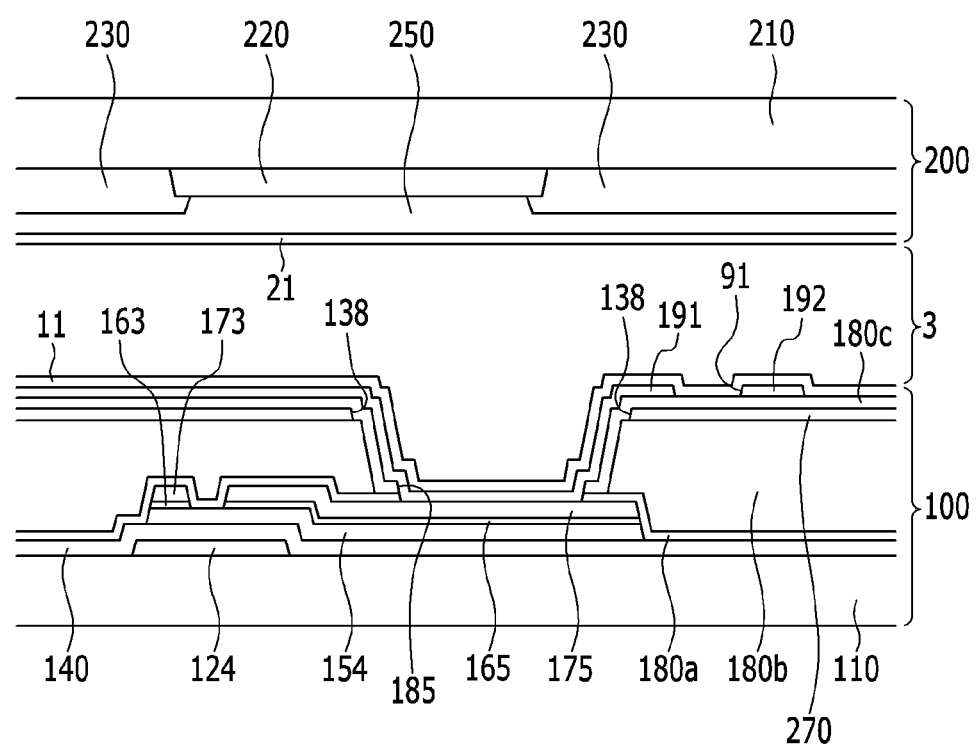
FIG. 2 is a cross-sectional view of FIG. 1, taken along the line II-II'.

FIG. 1 is a top plan view of a liquid crystal display according to an exemplary embodiment of the present invention. FIG. 2 is a cross-sectional view of FIG. 1, taken along the line II-II.

Referring to FIG. 1 and FIG. 2, a liquid crystal display according to the present exemplary embodiment includes a lower panel 100, an upper panel 200, and a liquid crystal layer 3. The lower panel 100 and the upper panel 200 are disposed facing each other, and the liquid crystal layer 3 is disposed between the two panels 100 and 200.

First, the lower panel 100 will be described.

A gate conductor including a gate line 121 is formed on a first substrate 110 made of transparent glass or plastic. The gate line 121 may include a wide end portion (not shown) for connection with another layer or an external driving circuit. The gate line 121 may be made of an aluminum-based metal such as aluminum (Al) or an aluminum alloy, a silver-based metal such as silver (Ag) or a silver alloy, a copper-based metal such as copper (Cu) or a copper alloy, a molybdenum-based metal such as molybdenum (Mo) or a molybdenum alloy, chromium (Cr), tantalum (Ta), and titanium (Ti). The gate line 121 may have a multilayered structure including at least two conductive layers having different physical properties.

A gate insulating made of a silicon nitride (SiNx), a silicon oxide (SiOx), or the like may be formed on the gate conductors 121 and 124. The gate insulating layer 140 may have a multilayered structure including at least two insulating layers having different physical properties. A semiconductor 154 made of amorphous silicon, polysilicon, or the like is formed on the gate insulating layer 140. The semiconductor 154 may include an oxide semiconductor.

Ohmic contacts 163 and 165 may be positioned on the semiconductor 154. The ohmic contacts 163 and 165 may be made of a material such as n+ hydrogenated amorphous silicon, in which an n-type impurity such as phosphorus is doped at a high concentration, or a silicide. The ohmic contacts 163 and 165 may be disposed on the semiconductor 154 to form a pair. When the semiconductor 154 is an oxide semiconductor, the ohmic contacts 163 and 165 may be omitted.

A data conductor including a drain electrode 175 and a data line 171 including a source electrode 173 is positioned on the ohmic contacts 163 and 165 and the gate insulating layer 140. The data line 171 includes an end portion (not shown) for connection with another layer or an external driving circuit. The data line 171 transfers a data signal, and substantially extend in a vertical direction to cross the gate line 121.

The data line 171 may have a first curved portion with a curved shape, in order to acquire high transmittance of the liquid crystal display. Portions of the curved portion meet each other in a middle region of the pixel area to have a V shape.

The source electrode 173 is a part of the data line 171, and is disposed on the same line as the data line 171. The drain electrode 175 extends in parallel with the source electrode 173. Accordingly, the drain electrode 175 is parallel with the part of the data line 171.

The gate electrode 124, the source electrode 173, and the drain electrode 175 form one thin-film transistor (TFT) together with the semiconductor 154. A channel of the thin-film transistor is formed in the semiconductor 154 between the source electrode 173 and the drain electrode 175.

The liquid crystal display according to the present exemplary embodiment includes the source electrode 173 positioned on the same line as the data line 171 and the drain electrode 175 extending parallel with the data line 171, and as a result, a width of the thin-film transistor may be increased while an area occupied by the data conductor is not increased, thereby increasing an aperture ratio of the liquid crystal display.

The data line 171 and the drain electrode 175 may be made of a refractory metal such as molybdenum, chromium, tantalum, and titanium, or an alloy thereof, and may have a multilayered structure including a refractory metal layer (not illustrated) and a low resistance conductive layer (not illustrated). For example, the multilayered structure may include a double layer of a chromium or molybdenum (alloy) lower layer and an aluminum (alloy) upper layer, or a triple layer of a molybdenum (alloy) lower layer, an aluminum (alloy) middle layer, and a molybdenum (alloy) upper layer.

A first passivation layer 180a is disposed on the data conductors, the gate insulating layer 140, and an exposed portion of the semiconductor 154. The first passivation layer 180a may be made of an organic insulating material, an inorganic insulating material, or the like.

A second passivation layer 180b is disposed on the first passivation layer 180a. The second passivation layer 180b may be formed of an organic insulator.

The second passivation layer 180b may be a color filter. When the second passivation layer 180b is a color filter, the second passivation layer 180q may display one of the primary colors such as red, green, or blue. The primary colors may include yellow, cyan, and magenta. Although not illustrated, the color filter may further include a color filter displaying a mixed color of the primary colors or white in addition to the primary colors. When the second passivation layer 180b is a color filter, the color filter 230 may be omitted in the upper panel 200. According to a modified embodiment of the present invention, the second passivation layer 180b may be formed of an organic insulating material and a color filter (not shown) may be disposed between the first passivation layer 180a and the second passivation layer 180b.

A common electrode 270 is disposed on the second passivation layer 180b. The common electrode 270 has a planar shape so as to be formed on the entire surface of the substrate 110 as a whole plate, and has an opening (not illustrated) formed in a region corresponding to a periphery of the drain electrode 175. More particularly, the common electrode 270 may have a planar shape in a plane view.

Common electrodes 270 disposed in adjacent pixels are connected to each other, so that a common voltage having a predetermined magnitude supplied from outside the display area is transmitted thereto.

An insulating layer 180c is disposed on the common electrode 270. The insulating layer 180c may be formed of an organic insulating material or an inorganic insulating material.

A pixel electrode 191 is disposed on the insulating layer 180c. The pixel electrode 191 includes a curved edge, which is substantially parallel to the first curved portion and the second curved portion of the data line 171. The pixel electrode 191 includes of cutouts 91 and branch electrodes 192 disposed between neighboring cutouts 91.

The pixel electrode 191 is a first field generating electrode or a first electrode, and the common electrode 270 is a second field generating electrode or a second electrode. The pixel electrode 191 and the common electrode 270 may form a fringe field.

A first contact hole 185 exposing the drain electrode 175 is formed in the first passivation layer 180a, the second passivation layer 180b, and the insulating layer 180c. The pixel electrode 191 is electrically connected with the drain electrode 175 through the contact hole 185 such that a voltage is applied thereto from the drain electrode 175.

A first alignment layer 11 is formed on the pixel electrode 191 and the insulating layer 180c. The first alignment layer 11 may be a horizontal alignment layer and is rubbed in a constant direction. The first alignment layer 11 may be a photoalignment layer.

Next, the upper panel 200 will be described.

A light blocking member 220 is disposed on a second substrate 210 made of transparent glass or plastic. The light blocking member 220 may be referred as a black matrix and blocks light leakage.

Color filters 230 are formed on the second substrate 210. When the second passivation layer 180b formed on the lower panel 100 is a color filter or when the color filter is formed in the lower panel 100, the color filters 230 of the upper panel 200 may be omitted. In addition, the light blocking member 220 of the upper panel 200 may also be formed in the lower panel 100.

An overcoat 250 is formed on the color filter 230 and the light blocking member 220. The overcoat 250 may be formed of an (organic) insulating material and prevent the color filters 230 from being exposed and provides a flat surface. The overcoat 250 may be omitted.

A second alignment layer 21 is disposed on the overcoat 250. The second alignment layer 21 may be formed of the same material as the first alignment layer 11.

The liquid crystal layer 3 is disposed between the lower panel 100 and the upper panel 200. In the present exemplary embodiment, the liquid crystal layer 3 is a liquid crystal material having positive dielectric anisotropy, and the above-stated liquid crystal composition may be applied.

The liquid crystal material of the liquid crystal layer 3 may be aligned such that the major axis thereof is disposed in parallel with the display panels 100 and 200.

The pixel electrode 191 receives a data voltage from the drain electrode 175, and the common electrode 270 receives a common voltage having a predetermined magnitude supplied from a common voltage applier disposed outside of a display area.

The pixel electrode 191 and the common electrode 270, which are field generating electrodes, generate an electric field such that liquid crystal of the liquid crystal layer 3 disposed on the two field generating electrodes 191 and 270 may be perpendicular to a direction of the electric field or rotate in a direction parallel with the direction of the electric field. The polarization of light passing through the liquid crystal layer may vary according to the determined rotation direction of the liquid crystal molecules.

As such, two field generating electrodes 191 and 270 are formed on the lower panel 100 to improve transmittance of the liquid crystal display and implement a wide viewing angle.

In the liquid crystal display according to the present exemplary embodiment, the common electrode 270 has a planar-shaped plane form and the pixel electrode 191 has branch electrodes. In a liquid crystal display according to an exemplary embodiment of the present invention, the pixel electrode 191 has a plane form of a planar shape and the common electrode 270 may have branch electrodes.

The liquid crystal display according to exemplary embodiments of the present invention may be applied in a liquid crystal display, where two field generating electrodes overlap with each other on the first substrate 110 with the insulating layer disposed therebetween, the first field generating electrode formed below the insulating layer has the plane form of the planar shape, and the second field generating electrode formed on the insulating layer has the branch electrodes.

Polarizers (not shown) may be provided on outer surfaces of the display panels 100 and 200, and polarization axes of the two polarizers may cross each other. One of the polarization axes may be parallel with the gate line 121. In the case of a reflective liquid crystal display, one of the two polarizers may be omitted.

Hereinafter, a liquid crystal composition and properties thereof according to an exemplary embodiment of the present invention will be described. Table 1 represents a comparative example 1, Table 2 represents an exemplary embodiment 1, Table 3 represents a comparative Example 2, Table 4 represents an exemplary embodiment 2, and Table 5 represents a referential example.

TABLE 1

| Liquid crystal compound | Content (wt %) |
|---|---|
| 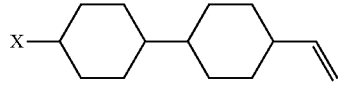 | 41.5 |
| 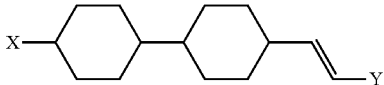 | 8 |
|  | 6.5 |
| 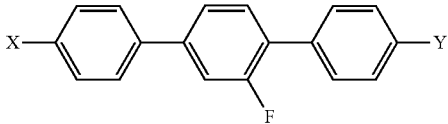 | 21 |
| 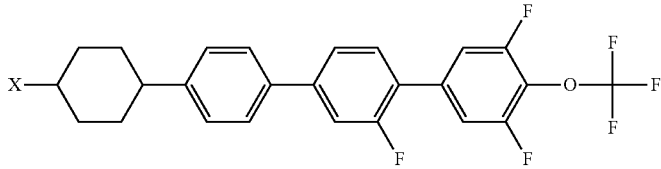 | 5 |
| 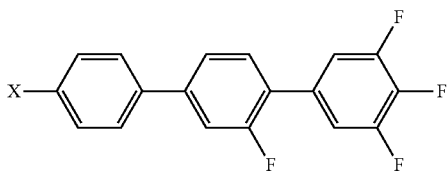 | 9 |

TABLE 1-continued

| Liquid crystal compound | Content (wt %) |
|---|---|
| 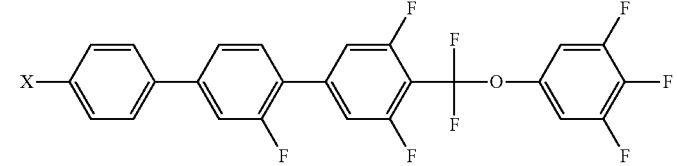 | 9 |

In Table 1, X and Y respectively include one alkyl group having 1 to 5 carbon atoms. The comparative example 1 includes compounds represented by Chemical Formula A-1, Chemical Formula A-2, Chemical Formula A-5, Chemical Formula N-3, Chemical Formula P-7, Chemical Formula P-8, and Chemical Formula P-11, but may not include compounds represented by Chemical Formula PI-1 to Chemical Formula PI-4 among the liquid crystal compounds according to an exemplary embodiment of the present invention. According to a property evaluation with respect to the comparative example 1, a refractive index Δn is about 0.12 to 0.14, dielectric anisotropy Δ∈ is about 4.9 to 5.1, and rotational viscosity γ1 is about 55 to 65.

TABLE 2

| Liquid crystal compound | Content (wt %) |
|---|---|
| 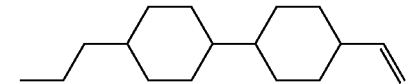 | 43.5 |
| 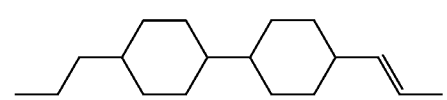 [SMILES: C/C=C/C1CCC(C2CCC(CCC)CC2)CC1] | 9 |
| 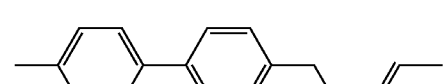 | 6.5 |
| 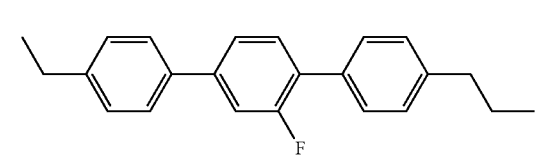 [SMILES: CCCc1ccc(-c2ccc(-c3ccc(CC)cc3)cc2F)cc1] | 6 |
| 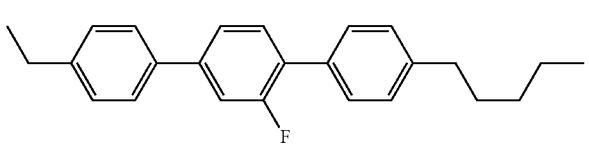 [SMILES: CCCCCc1ccc(-c2ccc(-c3ccc(CC)cc3)cc2F)cc1] | 6 |
| 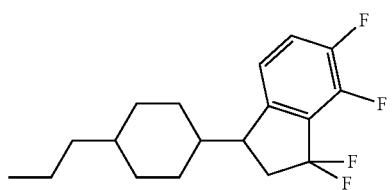 [SMILES: CCCC1CCC(C2CC(F)(F)c3c2ccc(F)c3F)CC1] | 3 |
| 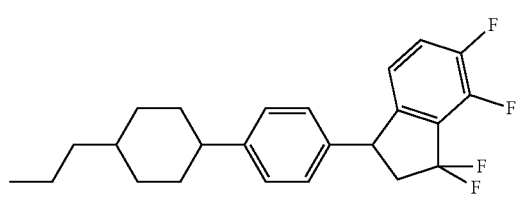 [SMILES: CCCC1CCC(c2ccc(C3CC(F)(F)c4c3ccc(F)c4F)cc2)CC1] | 3 |

TABLE 2-continued

| Liquid crystal compound | Content (wt %) |
|---|---|
| 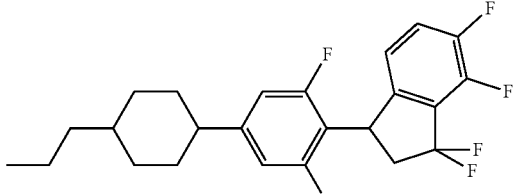 | 5 |
| 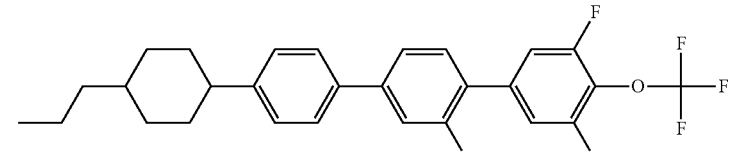 | 4 |
| 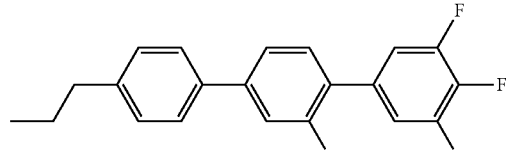 | 7 |
| 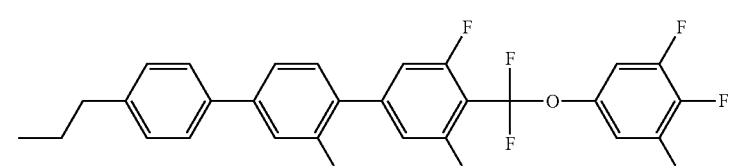 | 7 |

The exemplary embodiment 1 includes the compounds represented by Chemical Formula 2, Chemical Formula 4, and Chemical Formula 7 among the liquid crystal composition according to an exemplary embodiment of the present invention.

According to a property evaluation of the exemplary embodiment 1, a refractive index Δn is about 0.127, dielectric anisotropy Δ∈ is about 5.5, and rotation viscosity γ1 is about 59. A result of the property evaluation indicates that properties required in a conventional liquid crystal composition may be satisfied, even though a part of the terphenyl-based liquid crystal compound represented by Chemical Formula N-3 included in the comparative example 1 is omitted.

TABLE 3

| Liquid compound | Content (wt %) |
|---|---|
| 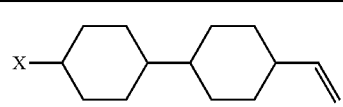 | 33 |
| 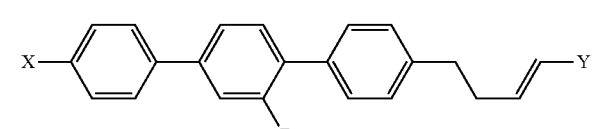 | 6 |

TABLE 3-continued

| Liquid compound | Content (wt %) |
|---|---|
| 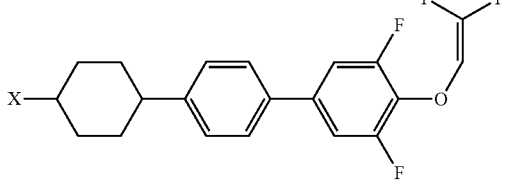<br>Chemical Formula A-8 | 12 |
| 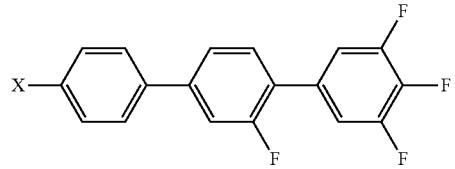 | 10.5 |
| 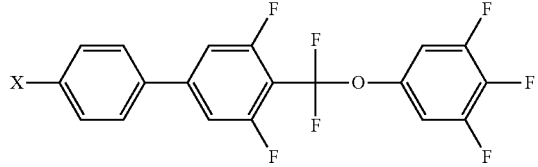 | 5 |
| 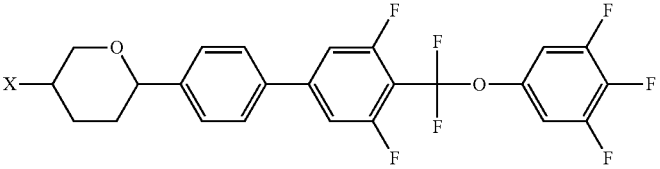 | 13.5 |
| 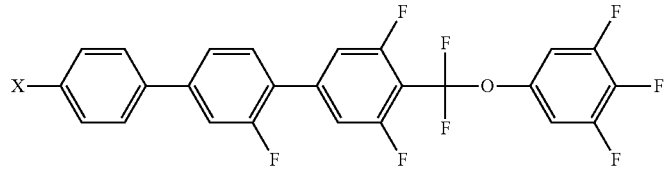 | 20 |

In Table 3, X and Y respectively include one alkyl group having 1 to 5 carbon atoms. The comparative example 2 includes compounds represented by Chemical Formula A-1, Chemical Formula A-6, Chemical Formula A-8, Chemical Formula P-8, Chemical Formula P-9, Chemical Formula P-10, and Chemical Formula P-11, but may not include compounds represented by Chemical Formula PI-1 to Chemical Formula PI-4 among the liquid crystal compounds according to an exemplary embodiment of the present invention. According to property evaluation with respect to the comparative example 2, a refractive index Δn is about 0.13 to 0.15, dielectric anisotropy Δ∈ is about 17.8 to 18.2, and rotation viscosity γ1 may be about 90 to 100.

TABLE 4

| Liquid crystal compound | Content (wt %) |
|---|---|
| 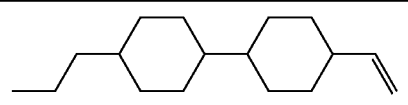 | 33 |
| 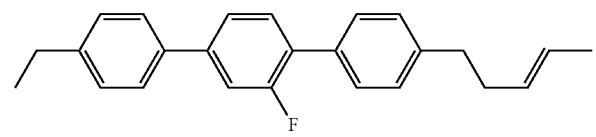 [SMILES: C/C=C/CCc1ccc(-c2ccc(-c3ccc(CC)cc3)cc2F)cc1] | 6 |

TABLE 4-continued
| Liquid crystal compound | Content (wt %) |
|---|---|
| 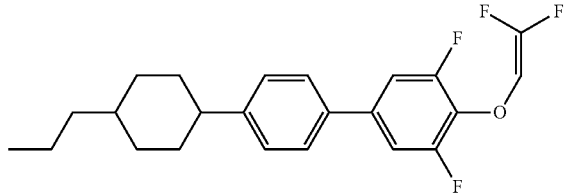<br>Chemical Formula A-8 | 12 |
| 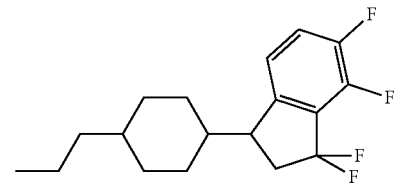 [SMILES: CCCC1CCC(C2CC(F)(F)c3c2ccc(F)c3F)CC1] | 4 |
| 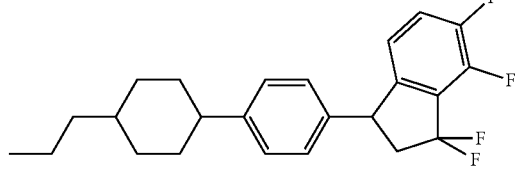 | 4 |
| 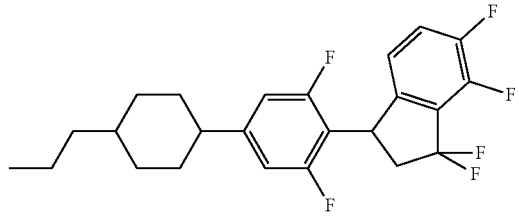 [SMILES: CCCC1CCC(c2cc(F)c(C3CC(F)(F)c4c3ccc(F)c4F)c(F)c2)CC1] | 4.5 |
| 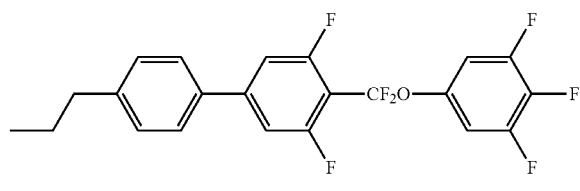 | 3 |
| 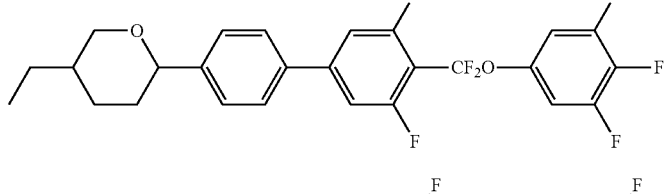 | 3 |
| 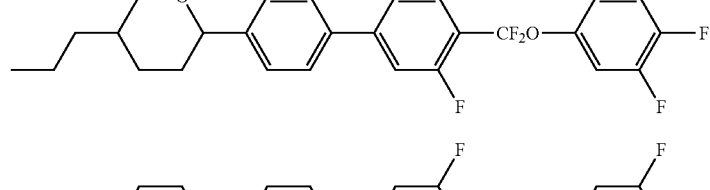 | 10.5 |
| 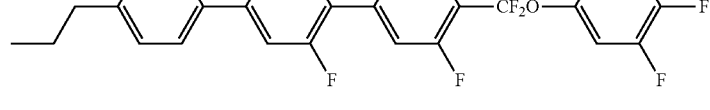 | 5 |

TABLE 4-continued

| Liquid crystal compound | Content (wt %) |
|---|---|
| [structure: propyl-phenyl-phenyl(2F)-phenyl(2F,6F)-CF₂O-phenyl(2F,3F,4F)] | 7 |
| [structure: butyl-phenyl-phenyl(2F)-phenyl(2F,6F)-CF₂O-phenyl(2F,3F,4F)] | 8 |

The exemplary embodiment 2 includes compounds represented by Chemical Formula 2, Chemical Formula 4, and Chemical Formula 6 among the liquid crystal compositions according to an exemplary embodiment of the present invention. However, an alkenyl-based liquid crystal compound, a neutral compound, and a polar compound mixed therewith are different from those of the exemplary embodiment 1.

According to a property evaluation of the exemplary embodiment 2, a refractive index $\Delta n$ is about 0.138, dielectric anisotropy $\Delta\varepsilon$ is about 17.8, and rotation viscosity $\gamma 1$ is about 90. The exemplary embodiment 2 is a liquid crystal composition that does not include a terphenyl-based liquid crystal compound represented by Chemical Formula P-8, and a liquid crystal composition including the liquid crystal compound according to the exemplary embodiment 2 has properties that the liquid crystal display requires.

Figure 3:
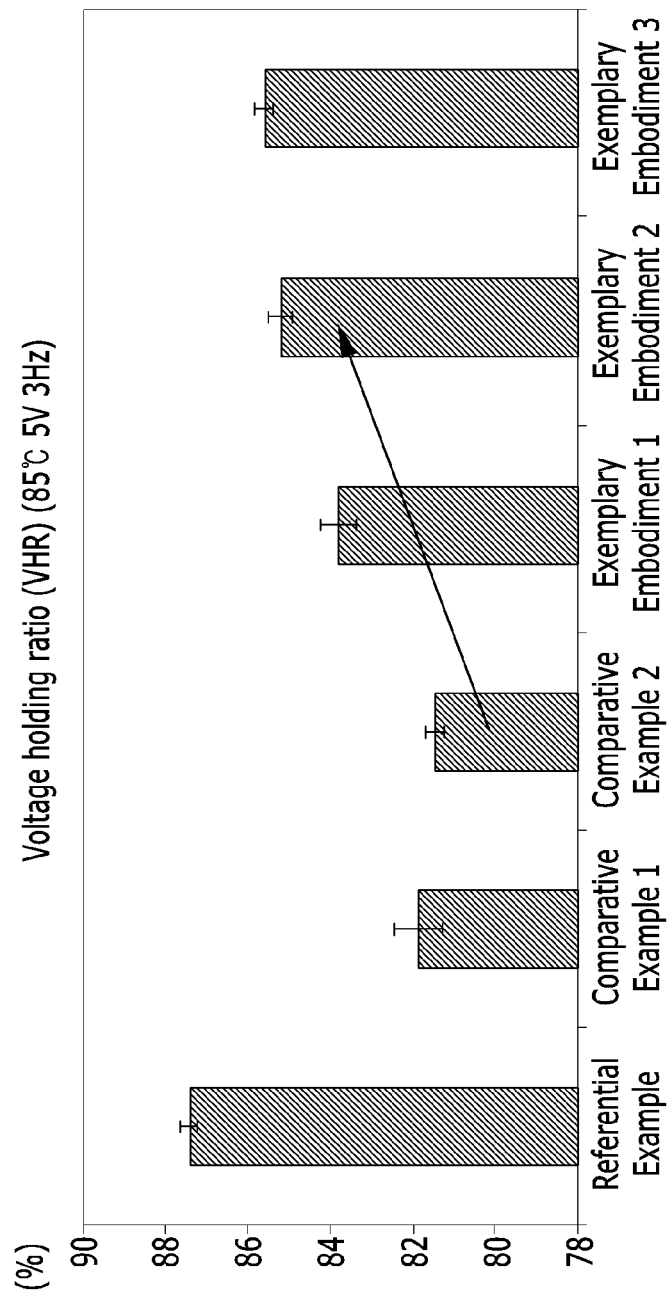
FIG. 3 is a graph illustrating a reliability improvement effect according on a voltage holding ratio of a liquid crystal display device using a liquid crystal composition according to an exemplary embodiment of the present invention.

FIG. 3 is a graph illustrating a reliability improvement effect according to a voltage holding ratio of the liquid crystal display, using the liquid crystal composition according to an exemplary embodiment of the present invention. In FIG. 3, a referential example is a liquid crystal display manufactured using a conventional liquid crystal composition shown in Table 1.

TABLE 5

| Liquid crystal compound | Content (wt %) |
|---|---|
| [propyl-cyclohexyl-phenyl-O–] | 25 |
| [butenyl-cyclohexyl-cyclohexyl-ethyl] | 15 |
| [propyl-cyclohexyl-cyclohexyl-phenyl] | 10 |
| [propyl-cyclohexyl-cyclohexyl-phenyl(3F,4F,5F)] | 15 |
| [butenyl-cyclohexyl-cyclohexyl-phenyl(3F,4F,5F)] | 15 |
| [propyl-cyclohexyl-phenyl-phenyl(3F,4F)] | 20 |

A comparative example 1 includes 15 wt % of Chemical Formula P-8a, which corresponds to a compound of Chemical Formula P-8, added to a conventional liquid crystal composition, and a comparative example 2 includes 15 wt % of Chemical Formula P-8b, which corresponds to a compound of Chemical Formula P-8, added to the conventional liquid crystal composition. An exemplary embodiment 1 includes 15 wt % of the compound of Chemical Formula 2 added to the conventional liquid crystal composition, an exemplary embodiment 2 includes 15 wt % of the compound of Chemical Formula 4 added to the conventional liquid crystal composition, and an exemplary embodiment 3 includes 15 wt % of the compound of Chemical Formula 6 added to the conventional liquid crystal composition. More particularly, the exemplary embodiments 1, 2, and 3 include a polyfluorinated indane based compound having a positive polarity added to the conventional liquid crystal composition, instead of adding the terphenyl-based liquid crystal compound.

Chemical Formula P-8a

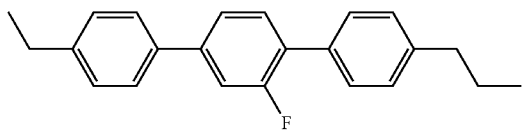

Chemical Formula P-8b

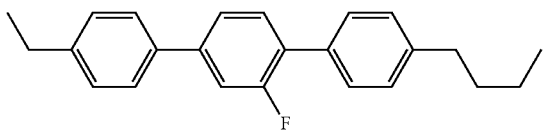

Referring to FIG. 3, the terphenyl-based liquid crystal compound is added in the comparative examples 1 and 2, such that a voltage holding ratio was reduced compared to the referential example. The terphenyl-based liquid crystal compound may generally increase a refractive index in a low cell gap to improve response speed, but may decrease reliability.

According to exemplary embodiments 1, 2, and 3 of the present invention, the liquid crystal composition includes the polyfluorinated indane based compound having a high dielectric constant, to have a low voltage characteristic, and a positive polarity to replace the terphenyl-based liquid crystal compound, to increase reliability.

Although certain exemplary embodiments and implementations have been described herein, other embodiments and modifications will be apparent from this description. Accordingly, the inventive concept is not limited to such exemplary embodiments, but rather to the broader scope of the presented claims and various obvious modifications and equivalent arrangements.

What is claimed is:

1. A liquid crystal composition, comprising:
at least one of polar liquid crystal compounds represented by Chemical Formula PI-1 to Chemical Formula PI-4:

Chemical Formula PI-1

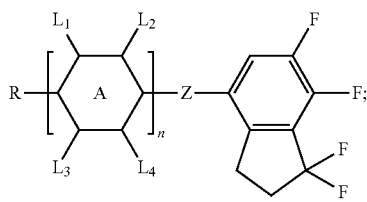

Chemical Formula PI-2

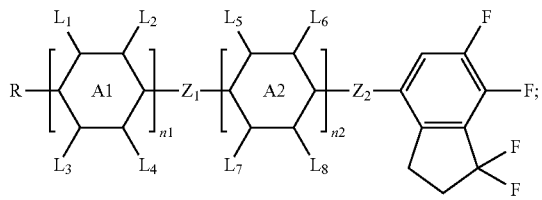

Chemical Formula PI-3

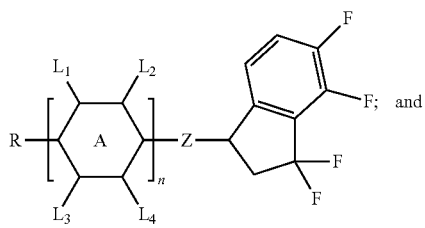

Chemical Formula PI-4

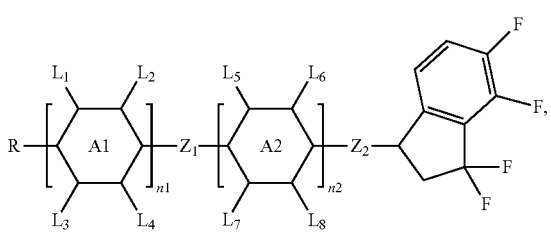

wherein each of n, n1, and n2 in Chemical Formula PI-1 to Chemical Formula PI-4 is any one of 1, 2, and 3,
wherein in Chemical Formula PI-1 to Chemical Formula PI-4, each of A, A1, and A2 comprises one of

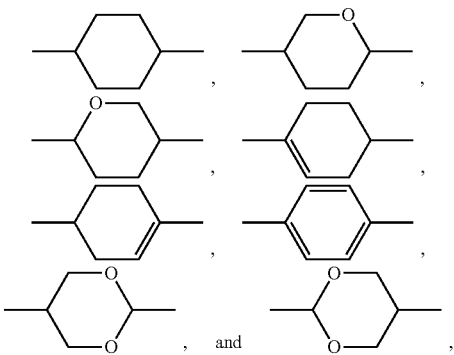

wherein in Chemical Formula PI-1 to Chemical Formula PI-4, each of L1 to L8 comprises one of —H, —F, —Cl, —OCF$_3$, —CF$_3$, —CH$_2$F, and —CHF$_2$,
wherein in Chemical Formula PI-1 to Chemical Formula PI-4, each of Z, Z1, and Z2 comprises one of single bond, —COO—, —OCO—, —CF$_2$O—, —OCF$_2$—, —CH$_2$O—, —OCH$_2$—, —SCH$_2$—, —CH$_2$S—, —CH$_2$CH$_2$—, —C$_2$F$_4$—, —CH$_2$—CF$_2$—, —CF$_2$CH$_2$—, —(CH$_2$)$_z$— (z is 1 to 3), —CH=CH—, —CF=CF—, —CH=CF—, —CF=CH—, —C≡C—, and —CH=CHCH$_2$O—, and
wherein in Chemical Formula PI-1 to Chemical Formula PI-4, R comprises one of hydrogen, halogen, a cyano group, alkyl group, and an alkoxy group comprising 1 to 12 carbon atoms.

2. The liquid crystal composition of claim 1, wherein compounds represented by Chemical Formula PI-1 to Chemical Formula PI-4 comprise 1 wt % to 10 wt % of the entire liquid crystal composition.

3. The liquid crystal composition of claim 1, wherein dielectric anisotropy Δ∈ of the polar liquid crystal compounds represented by Chemical Formula PI-1 to Chemical Formula PI-1 is in a range of 10 to 30.

4. The liquid crystal composition of claim 1, further comprising at least one liquid crystal compound represented by Chemical Formula A-1 to Chemical Formula A-7:

Chemical Formula A-1
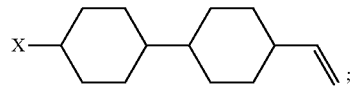

Chemical Formula A-2
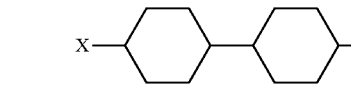

Chemical Formula A-3
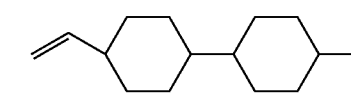

Chemical Formula A-4
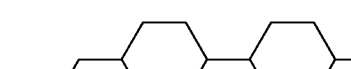

Chemical Formula A-5
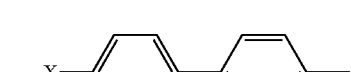

Chemical Formula A-6
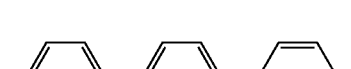

; and

Chemical Formula A-7

wherein each of X and Y in Chemical Formula A-1 to Chemical Formula A-7 comprises one alkyl group comprising 1 to 5 carbon atoms.

5. The liquid crystal composition of claim 4, further comprising at least one neutral compound represented by Chemical Formula N-1 to Chemical Formula N-5:

Chemical Formula N-1
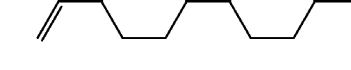

Chemical Formula N-2
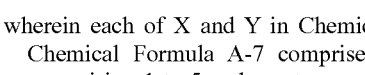

Chemical Formula N-3
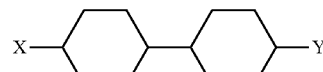

Chemical Formula N-4
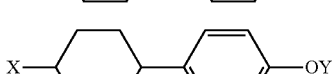

Chemical Formula N-5
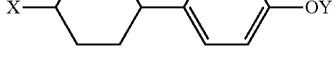

wherein each of X and Y in the Chemical Formula N-1 to Chemical Formula N-5 comprises one alkyl group comprising 1 to 5 carbon atoms.

6. The liquid crystal composition of claim 5, further comprising at least one polar compound represented by Chemical Formula P-1 to Chemical Formula P-11:

Chemical Formula P-1
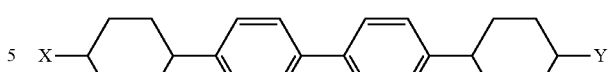

Chemical Formula P-2
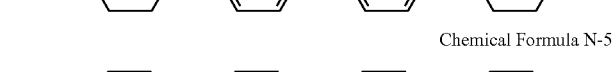

Chemical Formula P-3
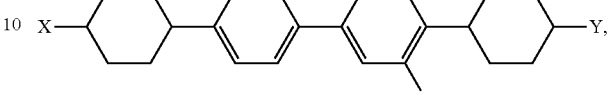

Chemical Formula P-4
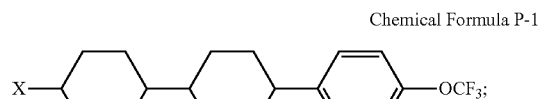

Chemical Formula P-5
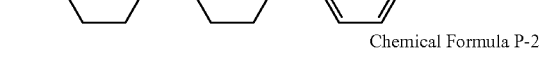

Chemical Formula P-6
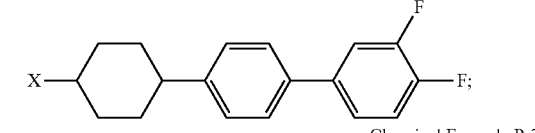

-continued

Chemical Formula P-7

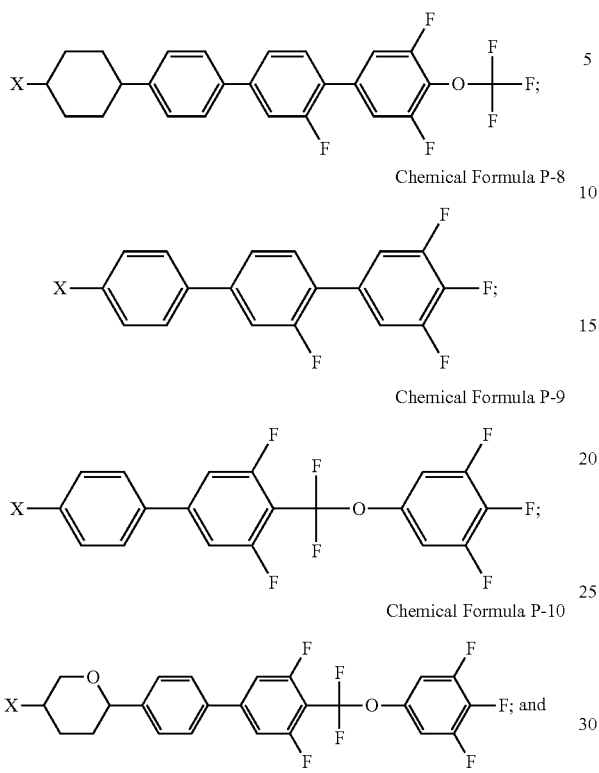

Chemical Formula P-8

Chemical Formula P-9

Chemical Formula P-10

Chemical Formula P-11 wherein each of X and Y in the Chemical Formula P-1 to Chemical Formula P-11 comprises one alkyl group comprising 1 to 5 carbon atoms.

7. A liquid crystal composition, comprising:
at least one of polar liquid crystal compounds represented by Chemical Formula PI-1 to Chemical Formula PI-4:

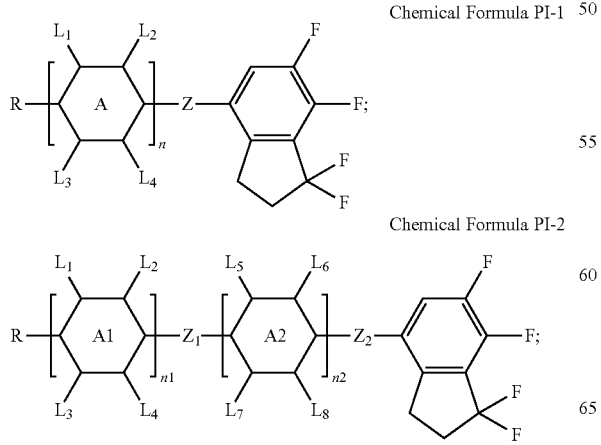

Chemical Formula PI-1

Chemical Formula PI-2

-continued

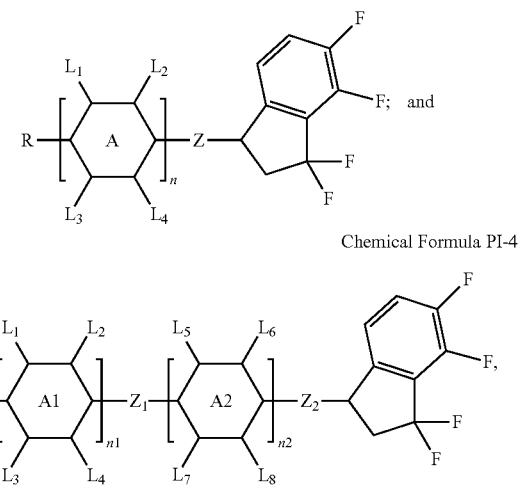

Chemical Formula PI-3

Chemical Formula PI-4 wherein each of n, n1, and n2 in Chemical Formula PI-1 to Chemical Formula PI-4 is any one of 1, 2, and 3, wherein in Chemical Formula PI-1 to Chemical Formula PI-4, each of A, A1, and A2 comprises one of

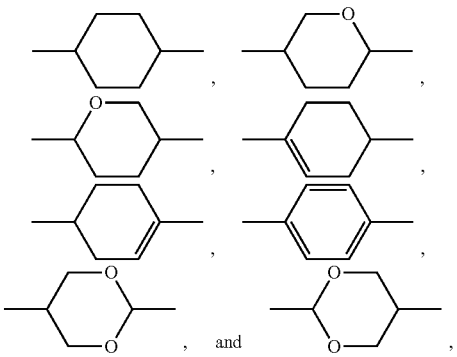

wherein in Chemical Formula PI-1 to Chemical Formula PI-4, each of L1 to L8 comprises one of —H, —F, —Cl, —OCF$_3$, —CF$_3$, —CH$_2$F, and —CHF$_2$, wherein in Chemical Formula PI-1 to Chemical Formula PI-4, each of Z, Z1, and Z2 comprises one of single bond, —COO—, —OCO—, —CF$_2$O—, —OCF$_2$—, —CH$_2$O—, —OCH$_2$—, —SCH$_2$—, —CH$_2$S—, —CH$_2$CH$_2$—, —C$_2$F$_4$—, —CH$_2$—CF$_2$—, —CF$_2$CH$_2$—, —(CH$_2$)$_z$— (z is 1 to 3), —CH=CH—, —CF=CF—, —CH=CF—, —CF=CH—, —C≡C—, and —CH=CHCH$_2$O—, wherein in Chemical Formula PI-1 to Chemical Formula PI-4, R comprises one of hydrogen, halogen, a cyano group, alkyl group, and an alkoxy group comprising 1 to 12 carbon atoms, and wherein dielectric anisotropy of the liquid crystal composition is in a range of 5 to 20.

8. A liquid crystal display, comprising:
a first substrate;
a second substrate facing the first substrate; and
a liquid crystal layer disposed between the first substrate and the second substrate,
wherein the liquid crystal layer comprises at least one polar liquid crystal compound represented by Chemical Formula PI-1 to Chemical Formula PI-4:

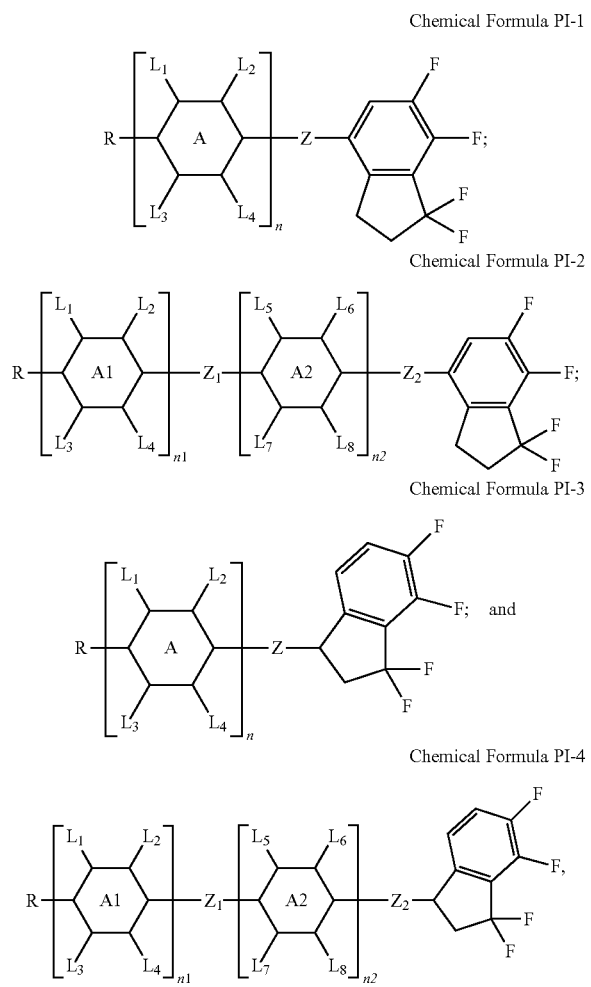

Chemical Formula PI-1

Chemical Formula PI-2

Chemical Formula PI-3

Chemical Formula PI-4 wherein in Chemical Formula PI-1 to Chemical Formula PI-4:
each of n, n1, and n2 is any one of 1, 2, and 3;
each of Z, Z1, and Z2 comprises one of single bond, —COO—, —OCO—, —CF$_2$O—, —OCF$_2$—, —CH$_2$O—, —OCH$_2$—, —SCH$_2$—, —CH$_2$S—, —CH$_2$CH$_2$—, —C$_2$F$_4$—, —CH$_2$—CF$_2$—, —CF$_2$CH$_2$—, —(CH$_2$)$_z$— (z is 1 to 3), —CH═CH—, —CF═CF—, —CH═CF—, —CF═CH—, —C≡C—, and —CH═CHCH$_2$O—; and
each of L1 to L8 comprises one of —H, —F, —Cl, —OCF$_3$, —CF$_3$, —CH$_2$F, and —CHF$_2$,
wherein in Chemical Formula PI-1 to Chemical Formula PI-4, each of A, A1, and A2 comprises one of

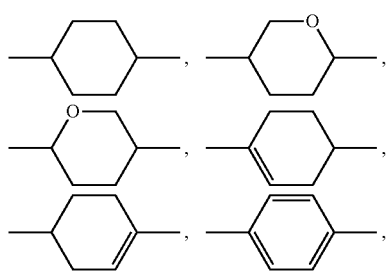

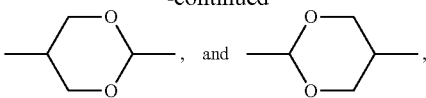

and wherein in Chemical Formula PI-1 to Chemical Formula PI-4, R comprises one of hydrogen, halogen, a cyano group, alkyl group, and an alkoxy group comprising 1 to 12 carbon atoms.

9. The liquid crystal display of claim 8, wherein compounds represented by Chemical Formula PI-1 to Chemical Formula PI-4 comprise 1 wt % to 10 wt % of the entire liquid crystal composition.

10. The liquid crystal display of claim 8, wherein dielectric anisotropy Δ∈ of the polar liquid crystal compounds represented by Chemical Formula PI-1 to Chemical Formula PI-4 is in a range of 10 to 30.

11. The liquid crystal display of claim 10, wherein the liquid crystal layer further comprises at least one liquid crystal compound represented by Chemical Formula A-1 to Chemical Formula A-7:

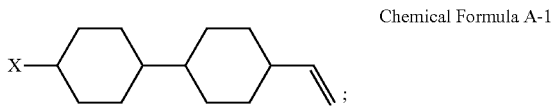

Chemical Formula A-1

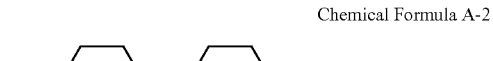

Chemical Formula A-2

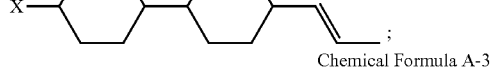

Chemical Formula A-3

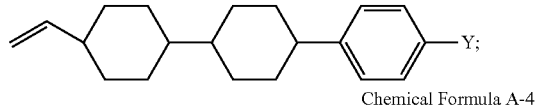

Chemical Formula A-4

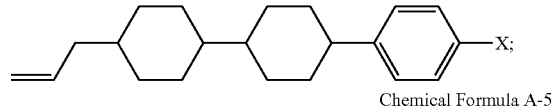

Chemical Formula A-5

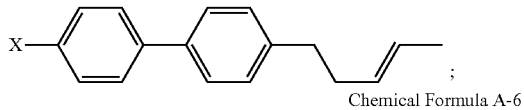

Chemical Formula A-6

; and

Chemical Formula A-7

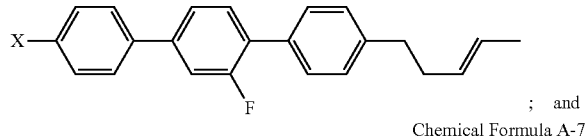

wherein each of X and Y in Chemical Formula A-1 to Chemical Formula A-7 comprises one alkyl group comprising 1 to 5 carbon atoms.

12. The liquid crystal display of claim 11, wherein the liquid crystal layer further comprises at least one neutral compound represented by Chemical Formula N-1 to Chemical Formula N-5:

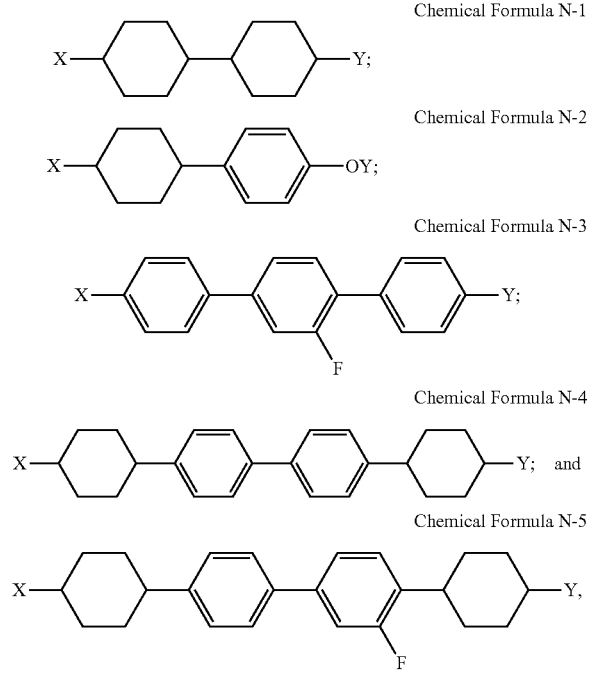

wherein each of X and Y in Chemical Formula N-1 to Chemical Formula N-5 comprises alkyl group comprising 1 to 5 carbon atoms.

13. The liquid crystal display of claim 12, wherein the liquid crystal display further comprises polar compounds represented by Chemical Formula P-1 to Chemical Formula P-11:

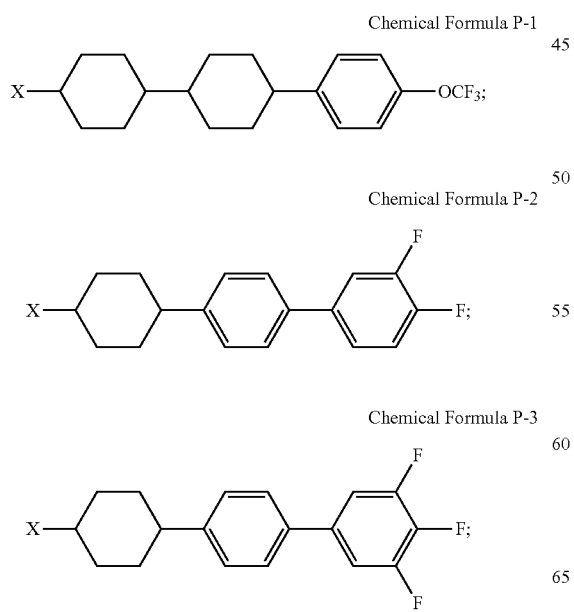

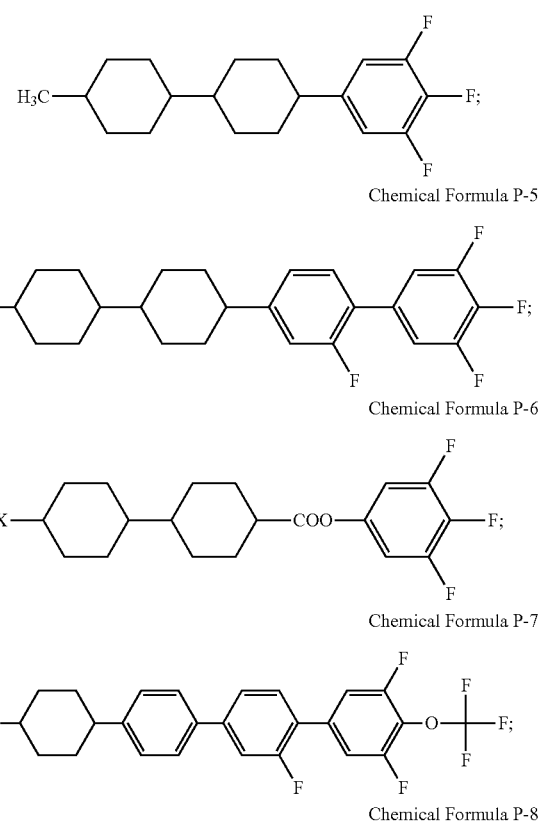

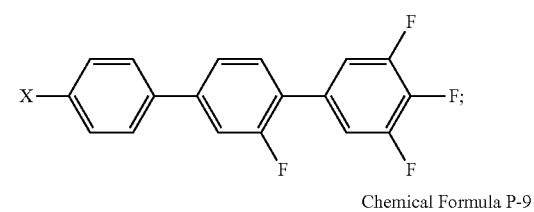

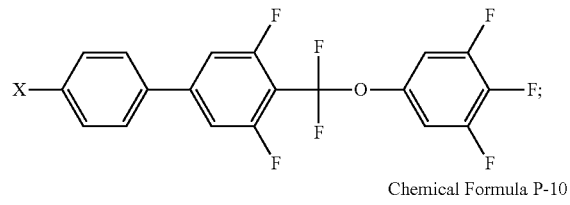

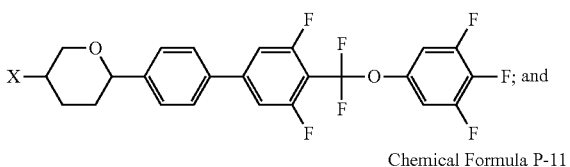

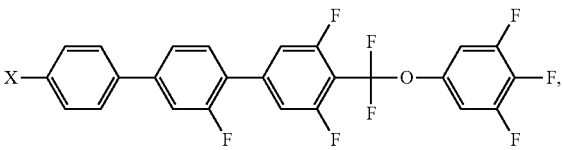

wherein each of X and Y in Chemical Formula P-1 to Chemical Formula P-11 comprises one alkyl group comprising 1 to 5 carbon atoms.

14. The liquid crystal display of claim 13, wherein dielectric anisotropy of the liquid crystal composition in the liquid crystal layer is in a range of 5 to 20.

* * * * *